United States Patent [19]

Chaudry et al.

[11] Patent Number: 5,583,121
[45] Date of Patent: Dec. 10, 1996

[54] NON-ANTICOAGULANT CHEMICALLY MODIFIED HEPARINOIDS FOR TREATING HYPOVOLEMIC SHOCK AND RELATED SHOCK SYNDROMES

[75] Inventors: Irshad H. Chaudry, East Lansing, Mass.; Kevin R. Holme, Alameda, Calif.

[73] Assignees: Michigan State University, East Lansing, Mich.; Glycomed Incorporated, Alameda, Calif.

[21] Appl. No.: 251,817

[22] Filed: May 31, 1994

Related U.S. Application Data

[63] Continuation-in-part of Ser. No. 180,585, Jan. 12, 1994, abandoned.

[51] Int. Cl.$^6$ .......................... A61K 31/725; C08B 37/10
[52] U.S. Cl. .................. 514/56; 514/921; 536/21
[58] Field of Search .......................... 514/56, 921; 536/21

[56] References Cited

U.S. PATENT DOCUMENTS

| | | | |
|---|---|---|---|
| 4,847,338 | 7/1989 | Lindhardt et al. | 536/54 |
| 4,916,219 | 4/1990 | Linhardt et al. | 536/21 |
| 4,990,502 | 2/1991 | Lormeau et al. | 514/56 |
| 5,034,520 | 7/1991 | Lormeau et al. | 536/127 |

FOREIGN PATENT DOCUMENTS

| | | |
|---|---|---|
| 0557887A2 | 9/1993 | European Pat. Off. . |
| 0565863A2 | 10/1993 | European Pat. Off. . |
| 0565862A2 | 10/1993 | European Pat. Off. . |
| WO9202232 | 2/1992 | WIPO . |

OTHER PUBLICATIONS

Sharath et al., Immunopharmacology (1985) 9:73–80.
Singh et al., The Journal of Trauma (1993) 34:5:645–652.
Wang et al., American Journal of Physiology (1990) 28:645–650.
Waheed et al., The Journal of Trauma (1992) 32:4:420–426.
Wang et al., Journal of Surgical Research (1993) 54:499–506.
Chaudry et al., The American Journal of Surgery (1993) 165:2A:59S–67S .
Chaudry et al., Immunologic Aspects of Hemmorhage (1992) Chapter 4:35–40.
Cotran et al., Robbins Pathologic Basis of Disease (4th Edition) 114–120.
Singh et al. Presentation and discussion at the Fifty–Second Annual Session of the American Association for the Surgery of Trauma, Sep. 17–19, 1992, Louisville, KY, as described in *J. Trauma* May 1993, 34(5), 645–652.
Rana et al. *J. Trauma* 1992, 32(4), 420–426.
"Dorland's Pocket Medical Dictionary" W. B. Saunders Co., 1989, pp. 539–540.
Hobson II et al. *Microcirc. Endoth. Lymphatics* 1989, 5, 259–276.
Deitch Discussion of the Singh et al. presentation (L) at the Fifty–Second Annual Session of the American Association for the Surgery of Trauma, Sep. 17–19, 1992, Louisville, KY, as described in *J. Trauma* May 1993, 34(5), 645–652.
Chaudry, et al, "A Clinically Relevant Model of Hemorrhagic Shock and Resuscitation in the Rat", Cir. Shock (1989) 27 318.
Chaudry et al., "Rat and Mouse Models of Hypovolemic-Traumatic Shock," Pathophysiology of Shock, Sesis, and Organ Failure (1993) pp. 371–383.

*Primary Examiner*—Douglas W. Robinson
*Assistant Examiner*—Kathleen Kahler Fonda
*Attorney, Agent, or Firm*—Lyon & Lyon

[57] ABSTRACT

A method of treating hypovolemic shock and related shock syndromes by the administration of substantially non-anticoagulant heparinoids without the hemorrhaging problems generally associated with heparin; such syndromes include degradation of the microvascular structure, immune and gastrointestinal tract dysfunction, and multiple organ failure.

19 Claims, 13 Drawing Sheets

○—○ = SHAM   △—△ = HEPARIN
●—● = SALINE  ▲—▲ = 2-0 NAC

○—○ = SHAM   △—△ = HEPARIN
●—● = SALINE  ▲—▲ = 2-0 NAC

NON-ANTICOAGULANT CHEMICALLY MODIFIED HEPARINOIDS FOR TREATING HYPOVOLEMIC SHOCK AND RELATED SHOCK SYNDROMES

This invention was made with government support under grant NIH-GM-39519 awarded by the National Institutes of Health. The government has certain rights in the invention.

This application is a continuation-in-part of U.S. patent application Ser. No. 08/180,585, filed Jan. 12, 1994, now abandoned.

FIELD OF THE INVENTION

The invention relates to treatment and prevention of a certain form of shock, hypovolemic shock and related syndromes with substantially non-anticoagulant chemically modified heparinoids. The heparinoids preserve the function of heart, liver, kidney and gut, protect microvasculature against degradation, and improve immune function following hemorrhage induced shock.

BACKGROUND OF THE INVENTION

Heparin and heparan sulfate

Heparan sulfate is a member of the glycosaminoglycan family of polysaccharides. These glycosaminoglycans are linear polymeric carbohydrate chains that are the glycan part of proteoglycan molecules that are important structural and functional components of the extracellular matrix.

Heparan sulfate and heparin like compounds share a biosynthetic pathway, and are characterized by a repeating disaccharide units consisting of a 2-amino-2-deoxy-D-glucose (glucosamine, GlcN) residue linked a-(1–4) to a uronic acid residue in a repeating fashion. The glucosamine can exist in the 2-acetamido-2-deoxy-D-glucose (GlcNAc), 2-deoxy-2-sulfamino-D-glucose (GlcNS) and 2-deoxy-2-sulfamino, 6-O-sulfate-D-glucose (GlcNS6S) forms. The uronic acid residue can be either β-D-glucuronic acid (GlcA) or α-L-iduronic acid (IdoA), the latter of which can exist in the 2-O-sulfated form (IdoA2S). The exact composition of heparan sulfates varies significantly depending on the source and even the specific stage of cell growth. Heparin has been shown to be a more extensively transformed biosynthetic form of heparan sulfate. Heparin possesses a greater proportion of the IdoA2S and GlcNS6S residues and is therefore a more highly sulfated substance. In-vivo heparin is found in association with mast cells, and not with the extracellular matrix of vascularized tissue, as is heparan sulfate.

Heparin is a commonly employed anticoagulant and antithrombotic drug. Commercial heparin is usually isolated from porcine or bovine mucosa, or bovine lung tissue. The anticoagulant action of heparin has been shown to reside largely in its ability to interact with and potentiate the activity of a circulating protein, antithrombin III (AT-III). AT-III is a serine protease inhibitor that inhibits many of the serine proteases involved in the coagulation cascade, particularly thrombin (Factor IIa) and Factor Xa. Heparin interacts with AT-III to form a complex that inhibits thrombin and Xa much more effectively than AT-III alone. Heparin interacts with AT-III through a specific high affinity pentasaccharide sequence that represents only a minor portion of any heparin chain. Heparin also interacts with another serine protease inhibitor, heparin cofactor II, to potentiate the inhibition of thrombin. The interaction with HC-II operates through different structural requirements and does not appear to have the same degree of specificity as the AT-III interaction.

The potent anticoagulant related activities of heparin, unfortunately, preclude its use for many of the other potential indications. In particular, the anticoagulant activity of heparin can lead to hemorrhage and bleeding complications when administered at doses that yield other therapeutic benefit. This factor has led to an interest in selectively decoupling the anticoagulant activity of heparin from other biological properties of the molecule. This decoupling strategy can also be applied to selectively decoupling or retaining other desirable biological and therapeutic properties. More selective agents would have reduced risk of toxic and/or contra-indicative effects. Also, the specificity could enhance overall bioavailability and potency of the agent relative to heparin.

Heparin/heparan sulfate have been shown to interact with a large and expanding number of proteins, and have been associated with numerous biological functions and activities. This poly-pharmacy is mediated by the ability of heparin-like materials to bind and inhibit or stimulate the action of a myriad of extracellular matrix resident and circulating receptors, proteins and enzymes. The broad pharmacological action of heparin and related compounds are of considerable therapeutic interest for a large number of indications, particularly in cardiovascular related diseases. There is considerable precedent for the utility of heparin based therapeutics for disease states related to hemostasis and thrombosis, and a recently expanding interest in conditions related to atherosclerosis, angiogenesis, metastasis and inflammation.

There is a fairly large effort in developing heparin based therapies for treating thrombotic and proliferative vascular disorders. However, despite considerable in-vitro, and anecdotal in-vivo evidence there has been relatively less focus on the anti-inflammatory use of heparin derived materials. Some of the anti-inflammatory properties of heparin derived compounds include; inhibition of complement activation, inhibition of heparanase dependent T-lymphocyte migration, inhibition of leukocyte platelet interaction. In addition, heparin and derivatives have shown activity in animal models of DTH, EAE, ischemia reperfusion and asthma, as well as anecdotal description of benefit in humans suffering from asthma and ischemia (myocardial infarction).

As mentioned above, its potent anticoagulant activity makes unattractive its therapeutic use for cardiovascular disorders. In particular, the anticoagulant activity of heparin leads to hemorrhage and bleeding complications when administered in therapeutic doses.

Pathology of shock

In general, shock can be described as widespread hypoperfusion of cells and tissue due to reduction in blood volume or cardiac output or redistribution of blood resulting in an inadequate effective circulating volume. Shock is usually classified into tour types: (1) Cardiogenic; (2) Hypovolemic; (3) Septic and (4) Neurogenic, largely on the basis of the hemodynamic derangement that leads to the condition. Extensive study has resulted in an understanding of the general mechanisms that lead to the pathology associated with shock. However, the myriad of biochemical processes that mediate the pathology are only just beginning to be understood. This relates to a complex cascade of inflammation-related events that have been studied in association with hypovolemic and septic shock that result in toxic injury to cell membranes of endothelial and other organ cells, leukocytes and platelets, activation of intrinsic and extrinsic coagulation pathways, complement activation and formation of the vasoactive and chemotactic fragments C5a and C3a.

Hypovolemic shock, (2), and models for studying this condition are described by Chaudry and Ayala in "Immunological Aspects of Hemorrhage" (R. G. Landes Co., Austin, Tex., 1992). Generally, hypovolemic shock due to reduced blood flow associated with blood loss results in "sludging" of the blood and capillary "plugging" by erythrocytes, platelets and neutrophils. This in turn leads to the insufficient delivery of oxygen and nutrients to cells and tissues, deficient clearance of other metabolites, and to activation of neutrophils and platelets. This oxidant stress (Hypoxia) and release of other factors from the endothelium and macrophages stimulates the arachidonic acid cascade and the production of chemoattractant and inflammation mediators, leading to further neutrophil infiltration. The activation of neutrophils, platelets, macrophages and the complement cascade leads to the release of numerous biologically active agents including cytokines. These factors stimulate expression of adhesion molecules on the surface of the endothelium, neutrophils and leukocytes which permit binding and ultimately migration of the neutrophils and leukocytes through the extracellular matrix (ECM) and basement membrane of blood vessels and capillaries. This migration or extravasation is attributed to the action of a number of extracellular matrix degrading enzymes including matrix metalloproteinases, serine proteases and endoglycosidases (i.e.hcparanases), which are released by activated neutrophils, leukocytcs and/or platelets. The damage to the ECM and basement membrane results in increased vascular permeability, and infiltration of organs by neutrophils and leukocytes.

An analogous series of events is associated with septic shock except, and most critically, the key mediators of the inflammatory response are unlikely to be the same as those that cause hypovolemic shock. The initial blood volume reduction in septic shock occurs as a result of blood pooling after endotoxin stimulate neutrophil activation and the release of inflammation mediating cytokines (TNF, IL-1 and IL-6, IL- 10, TGF-$\beta$, etc. ).

It is important to keep in mind that hypovolemic and septic shock are distinct diseases. Hypovolemic shock is a general collapse of the circulatory system that can be caused by many events including any trauma to the circulatory system (e.g. gun shot wound, automobile injury, burns, stabbing, and so on). Septic shock, on the other hand, is caused by bacterial infection. Thus, as mentioned above, the causes of these diseases are highly likely to be distinct.

Ischemia/reperfusion injury (FRD is another instance where inflammation mediated cell and organ damage result after a reduced blood flow state (ischemia).

The vascular damage associated with hypovolemic shock, and the resulting infiltration of neutrophils and leukocytes into the various organs leads to tissue damage and ultimately multiple organ failure (MOF) and acute respiratory distress syndrome (ARDS). The destructive agents and mediators are numerous and include cytokines, enzymes and various other inflammatory agents. MOF and ARDS can occur in severe shock and often result in death. For therapeutic agents to be effective in shock, they must protect the microvasculature and various organs (liver, kidney, heart, spleen and gut) from failure. The importance of protecting or restoring gut function and intestinal function in hemorrhagic shock and I/R injury has been reported, and correlates with reduced septic complications, and long-term survival.

Heparin and Shock

Chaudry et al. (*Am. J. Physiol.* 259 (Regulatory Integrative Comp. Physiol. 28) R645–R650, 1990 and *J. of Trauma* (1992) 32(4):420–426) have demonstrated that pre-heparinization can modulate the detrimental systemic effects that result from hypovolemic shock that can lead to MOF, and frequently death. This effect has been demonstrated in a rat hemorrhagic shock model (hypovolemic shock or traumatic shock) (Chaudry et al., *Circ. Shock* (1989) 27:318). This model differs from other hemorrhagic shock models mainly in that the animals are not heparinized prior to inducing shock, a situation that is more representative of the clinical situation. In this model, it was observed that pre-heparinized animals had significantly improved organ function relative to animals that were not heparinized but were otherwise subjected to hemorrhagic shock and resuscitated in the same manner. It was later shown that heparin administered during resuscitation had a similar beneficial effect, indicating that prior exposure to heparin was not necessary for protection.

The mechanism whereby heparin modulates the detrimental pathology of shock is not yet well understood. It is known that heparin and related heparan sulfate structures interact with a myriad of circulating proteins and enzymes, and a number of cell surface receptors. It may be that some of these interactions mediate shock damage. These biological activities and functions of heparin/heparan sulfate may depend on a number of chemical, compositional and physical characteristics, including: (1) saccharide composition; (2) functional group distribution; (3) charge density; (4) sulfate/carboxylate ratio; and (5) molecular weight. Regarding the latter, it has been demonstrated in the hemorrhagic shock model that the modulating effect of heparan is not directly related to the molecular weight of the heparin polymer, since a low molecular weight (LMW) heparin (average MW 3–4 kDa) had roughly equivalent effects. Chaudry et al., *Circ. Shock* (1991 ) 34:25).

In hypovolemic shock model studies with heparin that examined platelet function, it was concluded that the anticoagulant action of heparin may not be directly responsible for its action. Rana et al., *J. of Trauma* (1992) 32(4):420. This was supported by LMW heparin data, and by data obtained from a study using heparan sulfate, which has low anticoagulant activity, and which was found to be effective in preserving gut function after shock. Singh, et al., *J. of Trauma* (1993) 34:645.

Unfortunately, despite the work described above it is critical to keep in mind that none of these studies have elucidated the key structural requirements that a non-anticoagulant composition must have to be effective for treating or preventing hypovolemic shock.

Non-Anticoagulant (NAC) Heparin

Heparin's best known activity, its anticoagulant activity, prevents it from being used for a large number of possible clinical applications. Thus, considerable effort has been, and continues to be expended to identify heparin-like compounds for therapeutic use that have reduced anticoagulant activity and bleeding properties in vivo. Generally, two approaches have been pursued. The first being to identity forms of naturally occurring heparin that have lost anticoagulant activity. Included in this category are heparin fragments obtained by depolymerization and standard chromatographic separation methods, or by ATIII affinity fractionation. The second approach has been to chemically or enzymatically modify heparin to reduce its anticoagulant activity. In certain of these studies, heparin fragments may be prepared before or after chemical modification. Methods used for this latter approach include: (1) N-desulfation, N-modification; (2) N,O-desulfation and N-modification; (3) oversulfation; (4) carboxyl reduction or sulfation; and (5) periodate oxidation and reduction.

Not all of the above approaches to generating NAC heparins lead to compounds that fulfill the therapeutic criteria of low anticoagulant activity and limited effect on bleeding time when administered at therapeutically effective doses. Certain compositions may fulfill these criteria, but they also frequently lose the activity of interest. In other instances, the anticoagulant activity may be reduced, but the in vivo effect on bleeding remains elevated at useful doses. Some of these have been reported to be implicated in the inhibition of complement activation and C5a, in the inhibition of extracellular matrix degrading enzymes (elastase, cathepsin G and heparanases), and some have been proposed as useful for treating shock. See for example, U.S. Pat. No. 4,916,219 which describes anticomplement pharmaceutical compositions with reduced anticoagulant activity. The compositions consist of small chain fragments of heparin produced by the depolymerization of heparin with heparinase of from about 6 saccharide units to about 24 saccharide units. Although no data are presented, it was suggested that such compositions could be useful for treating septic shock. There is no description of using the compositions for treating hypovolemic shock.

It is important to keep in mind regarding NAC heparins that, in most instances, the precise requirements for specific heparin-related activities are not known, and that the activity of modified heparins is not predictable.

An example of non-anticoagulant depolymerized low molecular weight heparin is described in U.S. Pat. No. 4,990,502. It shows the treatment of heparin with periodate, followed by depolymerization with base, and reduction of the aldehydes generated in the periodate treatment. The resulting material is said to contain a mixture of polymers containing 17–33 residues and containing a multiplicity of residues of the formula

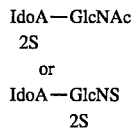

wherein the glucosamine residue is sulfated at the 3 and/or 6 position in an arbitrary manner, and wherein some of the IdoA residues may be replaced by cleaved IdoA or GlcA residues resulting from the periodate oxidation. These shortened polymeric chains are said to lack the binding site for ATIII but to be capable of inhibiting smooth muscle proliferation and to have physiological activities that include acceleration of tissue repair, prevention of atherogenous lesions, and prevention of the development of metastasis. Such compositions are also stated to be useful for the prevention of states of shock. There is, however, no discussion of using such compositions for treating hypovolemic shock.

Treatment of heparin/heparan sulfate with periodate has also been reported by others. For instance, Fransson, L. -A. and Lewis, W., *FEBS Lett* (1979) 97:1 19–123, describe a variety of conditions relating to the treatment of heparin/heparan sulfate with periodate and reduction by sodium borohydride or fragmentation in alkaline medium. Further, Fransson, L. -A. et al., *Carbohydrate Res* (1980) 80:131–145, studied the chemistry of various forms of heparin produced with periodate. In one study, the treatment with periodate was followed by β-elimination in base to produce fragmentation. They further reported the treatment of heparin with periodate followed by partial acid hydrolysis which results in fragmentation of the chains and partial destruction of the functional groups.

Another example of a non-anticoagulant heparin is described by Casu, B. et al., *Arzneim Forsch/Drug Res* (1986) 36:637–642. They studied the effect of periodate oxidation on the anti-lipemic (lipoprotein lipase-releasing) activity of heparin. In this study, the heparin was oxidized with periodate and the products were reduced with borohydride. Although the authors stated that the product has the same molecular weight as the starting material, it is apparent from the figures presented in the paper that there is significant depolymerization.

PCT/SE92/00243 shows a non-anticoagulant heparin that has a molecular weight larger than the heparin starting material, and that is produced by periodate oxidation, partial depolymerization by alkali, and subsequent borohydride reduction.

PCT WO/92/17188, published Oct. 15, 1992 describes N-deacetylated heparinoids prepared by treating heparin with a reagent to effect N-deacetylation, then with periodate under conditions to effect complete conversion of vicinal-diols and vicinal OH/NH2 to aldehydes, and then reduction of the aldehydes to alcohols under conditions wherein fragmentation is prevented.

PCT WO/92/17187, published Oct. 15, 1992 describes NAC heparinoids prepared by oxidation of heparin/heparin sulfate with periodate to convert diols to dialdehydes and reduction of the resulting aldehydes all under conditions wherein fragmentation is prevented.

U.S. Pat. No. 4,847,338 describes certain heparin oligosaccharides with diminished anticoagulant activity compared to heparin produced by the depolymerization of heparin with heparinase. Although no data are presented, such fragments are stated to be useful for the treatment of septic shock and immune disorders.

The 2-O desulfated heparin compositions described by Jaseja, M., et al., in *Can. J. Chem.* (1989) 67:1449–1456, have non-anticoagulant activity.

Of the NAC heparins described above only fragments generated from heparin, either by periodate oxidation followed by base depolymerization or depolymerization with heparinase, have been suggested to be therapeutically useful for the treatment of shock or shock related syndromes. See U.S. Pat. Nos. 4,916,219 and 4,990,502. No data are presented, however, that actually show that these compositions have such activity. That such compositions might be useful to treat shock is premised solely on their anti-complement activity. No correlation was shown with this activity and beneficial effects for treating shock or shock related syndromes. It is worth noting that inhibition of complement activation prevents the formation of the complement fragments C5a and C3a. These fragments are one of at least a dozen different mediators thought to be involved in shock. To date the mere inhibition of the formation of C5a and C3a has not be shown to be beneficial for the treatment of septic shock. Moreover, there is no description of using the compositions for treating hypovolemic shock.

Unlike the reports described above, to date there are no reports on NAC heparin compositions consisting of substantially undepolymerized polymer produced by chemical modification of heparin that are useful for the treatment of hypovolemic shock or shock related syndromes. Furthermore, there are no reports on the types of NAC heparin fragments that would be useful for such treatment that result from the depolymerization of chemically modified heparin, or that are produced by direct chemical modification of heparin fragments.

It will be appreciated that the availability of additional NAC heparin compositions that can be beneficially applied to treating hypovolemic shock or shock related syndromes will afford the physician a wider range of drugs to treat these diseases.

SUMMARY OF THE INVENTION

A first object of the invention is the description of a method for treating hypovolemic shock or shock related syndromes by administering an effective amount of certain chemically modified heparinoid compositions that substantially lacks anticoagulant activity.

A second object of the invention is the description of a method for treating hypovolemic shock by administering an effective amount of certain chemically modified heparinoid compositions that substantially lack anticoagulant activity wherein such compositions consist of substantially undepolymefized chemically modified heparin polymer.

A third object of the invention is the description of a method for treating hypovolemic shock by administering an effective amount of certain chemically modified heparinoid compositions that substantially lack anticoagulant activity wherein such compositions consist of modified heparin fragments.

A fourth object of the invention is the description of certain chemically modified heparinoid compositions useful for treating hypovolemic shock that substantially lack anticoagulant activity wherein the compositions are substantially N-sulfated or are not derived from hepafin by periodate oxidation followed by borohydride reduction.

A fifth object of the invention is the description of a method of obtaining therapeutically desirable results for certain individual clinical aspects of hypovolemic shock, shock syndromes, including the restoration of certain organ functions including the function of the heart, liver, kidney, gastrointestinal tract, or protecting the degradation of the microvascular structure and improving immune function. Such beneficial results may be realized alone or as part of a regime of NAC heparin administration as demonstrated herein.

These and other objects, advantages and features of the present invention will become apparent to those persons skilled in the art upon reading the details of the methodology and protocols described below, wherein reference is made to the accompanying figures forming a part hereof.

Abbreviations in the figures am defined as follows: "2-O NAC" represents 2-O desulfated NAC and "2-O,3-O NAC" represents 2-O, 3-O desulfated NAC.

Figure 11:
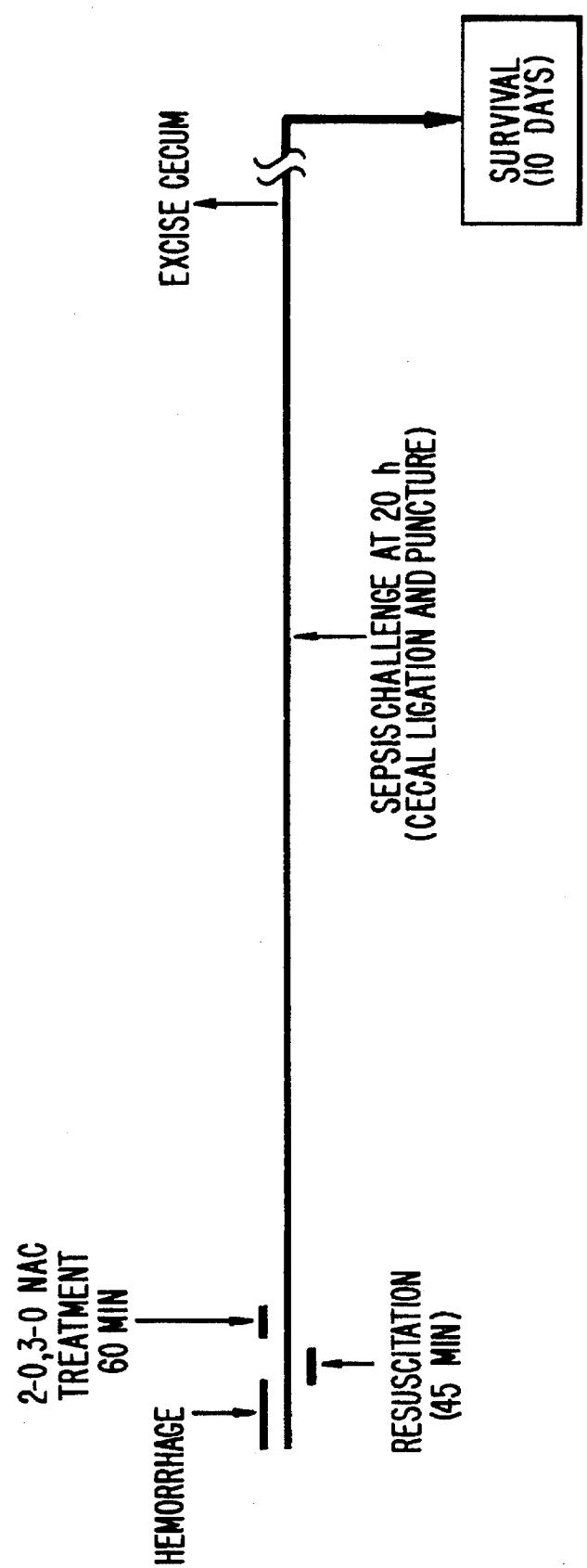

FIG. 11 shows the experimental design that was used in Example 5 to assess cardiovascular, hepatocellular function and mortality due to sepsis following trauma/hemorrhage and treatment with 2-O, 3-O desulphated NAC.

Figure 12:
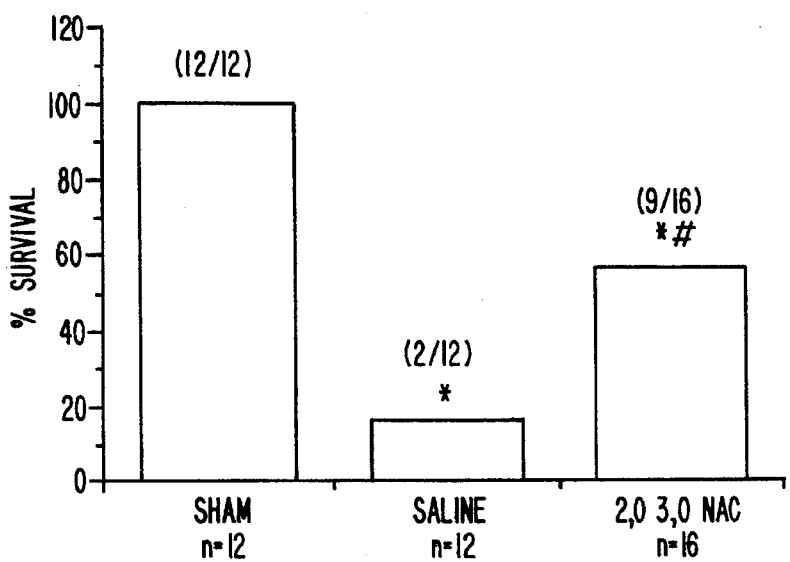

FIG. 12 shows the survival rate for animals treated according to the protocol described in Example 5.

DETAILED DESCRIPTION OF THE INVENTION

All publications and patent applications discussed or cited herein are understood to be incorporated by reference to the same extent as if each individual publication or patent application was specifically and individually set forth in its entirety.

Before the present method of treating hypovolemic shock or shock syndromes is disclosed and described, it is to be understood that this invention is not limited to the particular procedures and formulations described, as such may, of course, be varied as understood by the skilled practitioner of this art. It is also to be understood that the terminology used herein is for the purpose of describing particular embodiments only, and is not intended to be limiting, since the scope of the present invention will be limited only by the appended claims.

It must be noted that, as used in this specification and the appended claims, the singular forms "a," "an" and "the" include plural referents unless the context clearly dictates otherwise. Thus, for example, reference to "a heparinoid" includes mixtures of heparinoids, and reference to "the method" includes one or more equivalent methods of the general type disclosed and described herein, as would be apparent to those skilled in the art reading the present disclosure.

Understanding the invention will be facilitated by a brief discussion of certain of the technical terms used throughout the specification.

The terms "treating" and "treatment" are used interchangeably herein to define a methodology which is applied to an animal, preferably a human, suffering from one or more clinical manifestations of hypovolemic shock in order to prevent, reduce, or in some way ameliorate the adverse effects of shock. The mechanism of many diseases such as hypovolemic shock are complex and the result of multiple causes. Accordingly, "treating" as used herein indicates a methodology which interferes with one or more causes or events and thereby has a beneficial impact on the individual being treated. It is understood that to "treat" hypovolemic shock includes preventing, delaying or in some way reducing the onset of symptoms without perhaps actually removing the cause for shock completely. Accordingly, treatment with the present invention compositions may extend life and/or improve its quality even though the individual being treated ultimately succumbs to shock. The treatment in accordance with the present invention may encompass a single administration of a non-anticoagulant heparinoid compound or may involve several administrations of the compound over a period of time following adequate fluid resuscitation.

It is worth noting that while the invention methods are primarily focused on the treatment of hypovolemic shock they are also applicable to the prevention of such shock in patients that are at a high risk of developing the disease. For instance, certain conditions carry a high risk of developing hypovolemic shock including hemorrhage, trauma, burns, polyuria, vomiting, and diarrhea. See, *Circulatory Shock*, 91:7. Thus, a patient hospitalized for one of these conditions may be administered the compositions of the invention to prevent the development of hypovolemic shock. Consequently, while reference throughout the patent application is made to methods of treating hypovolemic shock it will be understood by the skilled practitioner of this art that such terminology encompasses preventing shock as well.

By "heparin/heparan sulfate" or "heparin" is meant a preparation obtained from tissues in a manner conventional for the preparation of heparin as an anticoagulant or otherwise synthesized and corresponding to that obtained from tissue. See Conrad, H. E., *Heparin and Related Polysaccharides*, Vol. 56, p. 18 of Annals of N.Y., Academy of Sc., Jun. 7, 1989, incorporated herein by reference. This preparation may include residues of D-glucuronic acid (GlcA), as characteristic of heparan sulfate as well as iduronic acid (IdoA) as characteristic of heparin. However, even though both GlcA and IdoA are present in both, they are present in different proportional amounts. The IdoA/GlcA ratio rises as heparan sulfate becomes more heparin-like. As described in the Background section above, the conversion of D-glucuronic acid to L-iduronic acid is a result of epimerization at the 5 carbon of GlcA residues in a heparan-type intermediate. This sequence of steps involved in such epimerization and conversion is understood in the art.

By hepafin fragments, or low molecular weight heparin, is meant heparin that has been treated with any one of a number of reagents and methods that depolymerize heparin preparations that have average molecular weights in the range of 5–30 kDa to compositions that have average molecular weights in the range of 2–6.5 kDa. Such reagents and methods are known in the art, and examples would include nitrous acid depolymerization, benzylation followed by alkaline depolymerization, peroxidative depolymerization, alkaline treatment, and enzymatic depolymerization with heparinase. See, Hirsh, J. and Levine, M., *Blood* (1992) 79:1–7, and U.S. Pat. No. 4,990,502 Low Molecular Weight. Heparins Of Regular Structure, Their Preparation And Their Biological Uses, Inventors Lormeau et al.; and U.S. Pat. No. 5,110,918, Process For Preparing EDTA-Free Heparins, Heparin Fractions And Fragments, Inventors Casu et al.

The "heparin/heparan sulfate" or "heparin" preparation can be obtained from a variety of mammalian tissues, including, if desired, human tissue. Generally, porcine or bovine sources are used, and vascularized tissues are preferred. A preferred source of heparin staring material is porcine intestinal mucosa, and preparations labeled "heparin" prepared from this tissue source are commercially available. In general, the heparin starting material is prepared from the selected tissue source by allowing the tissue to undergo autolysis and extracting the tissue with alkali, followed by coagulation of the protein, and then precipitation of the heparin-protein complex from the supernatant by acidification. The complex is recovered by reprecipitation with a polar nonaqueous solvent, such as ethanol or acetone or their mixtures, and the fats are removed by extraction with an organic solvent such as ethanol and proteins by treatment with a proteolytic enzyme, such as trypsin. Suitable procedures for the preparation of the heparin staring material are found, for example, in Charles, A. F., et al., *Biochem J* 30:1927–1933, and modifications of this basic procedure are also known, such as those disclosed by Coyne, E., in *Chemistry and Biology of Heparin.* (1981) Elsevier Publishers, North Holland, N.Y., Lunblad, R. L., et al., eds.

"NAC" and "NAC compositions" are used interchangeably herein to refer to non-anticoagulant heparinoids. NAC compositions are heparin, heparin fragments which have some of the properties of heparin, but are substantially non-anticoagulant. Specifically, the NAC compositions of the invention are chemically modified heparin or heparin fragments or derivatives thereof which have a substantially reduced anticoagulant activity as compared to heparin, as revealed by standard assay procedures, and as compared to commercial heparin. Preferably, such NAC compounds lack about 85% of the anticoagulant activity of heparin.

"Intact" and "unfragmented" are used interchangably to refer to NAC compositons that are substantially undepolymerized relative to the starting heparin material. Usually depolymerization is less than 10%.

Finally, as stated herein the NAG compounds are produced by chemical modification of heparin. It will be understood that such "chemical modification" can be by direct chemical reaction of heparin with the appropriate reagents and reaction conditions, enzymatic reaction, the use of genetically engineered cells, etc., and, indeed is intended to include any means whereby heparin is modified to the desired NAC compound. Also intended to come within this definition are NAC compounds obtained by affinity fractionation using heparin binding proteins wherein the fractions so obtained are NAC compositions. An example of this would be NAC compositions obtained by ATIII affinity fractionation.

Abbreviations

The following abbreviations are used for monosaccharides or for monosaccharide residues included in oligomers: D-glucuronic acid=GlcA; L-iduronic acid=IdoA; D-glucosamine=GlcNH$_2$; N-acetyl-D-glucosamine=GlcNAc; D-glucosamine N-sulfate=GlcNS; 2,5-anhydromannose= Aman; 2,5-anhydromannitol =AManHh.

Abbreviations that are used to denote disaccharide residues obtained in the analysis of heparin compositions described herein are as follows: ISMS is defined as IdoA (2-sulfate)—AManH (6-sulfate); GMS$_2$ is defined as GlcA—AManH (3,6-disulfate); IS defined as IdoA (2-sulfate)—AManH (6-sulfate)+IdoA (2-sulfate)—AManH.

In designating each saccharide residue, below the appropriate abbreviation, the location of the O-linked sulfate residues is indicated by "S" and the number of the position of sulfation where the sulfate residue is linked to oxygen on the sugar residue. In the designations for heparin structure, also, the positions involved in the alpha and beta anomeric linkages are as those conventionally found in heparin, —(glucosamine-uronic) and—(uronic-glucosamine), and the D or L configurations as conventionally found pertains. The locations of the sulfates are shown below the abbreviation for the sugar to which they apply, thus, for example, IdoA—GlcNS
2S   6S refers to a disaccharide composed of L-iduronic acid and D-glucosamine N-sulfate-linked-(1–4) with sulfates connected respectively at the 2 and 6 positions of the sugar residues.

In its most general form the instant invention is a method of treating hypovolemic shock or shock related syndromes by administering to an animal in need thereof an effective amount of certain heparinoids that substantially lack anticoagulant activity.

NAC compounds can be obtained by a variety of procedures and are generally but not exclusively obtained by beginning with commercial heparin (generally porcine or bovine derived) and thereafter carrying out one or more of the following procedures: (1) depolymerization; (2) N-desulfation, N-modification; (3) O-desulfation; (4) N,O-desulfation and N-modification; (5) oversulfation; (6) carboxyl reduction; (7) periodate oxidation and reduction; and (8) ATIII affinity fractionation. See PCT patent applications, WO 92/01003 and WO92/02232 which show certain non-anticoagulant heparins. The NAC compounds of the present invention can thus be obtained by subjecting heparin or heparin sulfate to one or more chemical treatments described herein. For example, depolymerization can be conducted in the presence of nitrous acid. Deacylation can be conducted by treatment with enzymes. PCT WO/92/17187-8 is incorporated herein by reference to disclose and describe such chemical treatment procedures.

Further examples of such NAC heparins include N-modified heparins that have been prepared from partially or completely N-deacetylated heparin (Y. Guo and H. E. Conrad, *Anal. Biochem.,* (1989) 176:96–104; and Shaklee and Conrad *Biochem J.* (1984) 217:187–197), followed by: (a) N-sulfation with appropriate N-sulfation reagents (L. Ayotte and A. S. Perlin, *Carbohydr. Res.* (1986) 145:267–277) to give analogues higher in sulfamino content and thus more anionic, (b) N-acylation with anhydrides (R(CO)$_2$O, where R=-(CH$_2$)$_n$H and aryl) to yield analogues having hydrophobic substituents that may enhance in binding to bioactive proteins by hydrophobic interaction. Additional N-modified analogues can be prepared by partial or complete N-desulfation of heparin (L. Ayotte and A. S. Periin, *Carbohydr. Res.* (1986) 145: 267–277) using known procedures, followed by re-N-acylation with arthydrides (R(CO)$_2$O, where R=-(CH$_2$)$_n$H and aryl)to yield heparin compositions with reduced artionic charge.

It is important to note that one aspect of the invention described herein is the unexpected discovery of certain characteristics and chemical properties that are preferred when selecting a NAC heparin composition to treat a patient for hypovolemic shock. For instance, we have discovered that substantially N-sulfated compositions are effacious as revealed by experiments which have shown that N-acetylated heparin is inactive. Second, certain substantially undepolymerized periodate oxidized, borohydride reduced NAC heparin compositions are also inactive. A composition, which was shown to be substantially inactive in the assays described below, is described in U.S. patent application Ser. No. 753,299, filed Sep. 3, 1991.

Thus, the NAC heparin compositions that have application in the instant invention are those that are substantially N-sulfated, and that are not substantially undepolymerized periodate oxidized, and borohydride reduced. Consequently, the definition of NAC or NAC heparin is intended to include all such compositions but this last class.

The 2-O, 3-O desulfated NAC heparin compositions described in U.S. patent application Ser. No. 944,804 are the preferred compositions. More preferred are the 2-O, 3-O desulfated heparin fragments described in the patent application. Because of their reduced size, such fragments exhibit very low anticoagulant activity, as well as have favored bioavailability and pharmacokinetic properties.

Administration of the non-anticoagulant heparinoids, including either substantially unfragmented 2-O, 3-O desulfated heparin, or 2-O, 3-O desulfated heparin fragments, is typically by routes appropriate for glycosaminoglycan compositions, and generally includes systemic administration, such as by injection.

Particularly preferred is intravenous injection, as continuous injection over long time periods can be easily continued. Also preferred is introduction into the vascular system through intraluminal administration or by adventitial administration using osmotic pumps or implants. Typical implants contain biodegradable materials such as collagen, polylactate, polylactate/polyglycoside mixtures, and the like. These may be formulated as patches or beads. Typical dosage ranges are in the range of 0.1–10 mg/kg/hr on a constant basis over a period of 5–30, preferably 7–14 days. A particularly preferred dosage is about 0.3 mg/kg/hr, or, for a 70 kg adult, 21 mg/hr or about 500 mg/day.

Other modes of administration are less preferred but can be more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular grail material, is particularly useful where the location of the trauma is accessible.

Formulations suitable for the foregoing modes of administration are known in the art, and a suitable compendium of formulations is found in *Remington's Pharmaceutical Sciences,* Mack Publishing Company, Easton, Pa., latest edition.

As mentioned above the preferred NAC non-anticoagulant heparinoid is a heparin derivative with a reduced level of sulfation and which differs from heparin, heparan sulfate and other modified heparins and heparinoids in that it contains substantially non-sulfated uronic acid residues (IdoA and GlcA), and possesses a fraction of the anticoagulant activity of heparin. It has efficacy in hypovolemic shock treatment equal to or greater than heparin. This heparin derivative is a composition of substantially unfragmented 2-O, 3-O desulfated heparin, or 2-O, 3-O desulfated heparin fragments. The methods described below, which are also disclosed in copending U.S. Ser. No. 07/994,804, filed Dec. 22, 1992, and also incorporated herein by reference, permit controlling the per cent of 2-O, 3-O desulfation.

EXAMPLES

The following examples are put forth so as to provide those of ordinary skill in the art with a complete disclosure and description of how to produce useful therapeutic heparinoid compositions and administer such in the treatment of hypovolemic shock, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described.

Example 1

Preparation of 2-O-Desulfated NAC Heparin

Heparin (1 g, 165 U/mg porcine mucosal, Ming Han) was dissolved in 200 ml of deionized water and adjusted to pH 12.8 using 1.0N NaOH. Water was then added to give a total volume of 250 ml and a final heparin concentration of 0.4%. The solution was then frozen and lyophilized to dryness. The crusty yellow residue was dissolved in 100 ml of de-ionized water and adjusted to pH 7 with 5% aqueous acetic acid. The solution was then dialyzed and lyophilized to give 0.8 g of final product.

The $^1$H-nmr spectrum of the product was consistent with reported characterization data for similarly prepared compounds (Jaseja et al, *Can J. Chem.,* 67,1449 (1889)). This supported that >90% of the 2-O-sulfated IdoA residues in the starting heparin were converted to non-sulfated IdoA residues in the product.

The anticoagulant properties of the product were 10–15% relative to the starting heparin (165 U/mg USP activity) as determined by aPTT coagulation assay.

Example 2

Effect of 2-O-desulfated NAC heparin on Hypovolemic shock in a Non-Heparinized Animal This experiment relates to non-anticoagulant heparinoids in treating hypovolemic shock when administered systemically (via i.v. injection, infusion or other appropriate route) during resuscitation following hemorrhage-induced shock in a non-heparinized animal. See, Chaudry et al., *Circ. Shock* (1989) 27:318. Subsequent articles have described the beneficial effects observed in this model when animals are pre-heparinized (Wang et al., *Am. J. physiol.,* 259 (Regulatory Integrative Comp. Physiol. 28) R645–R650, 1990 and Rana et al., *J. of Trauma* (1992) 32(4):420–426), and when heparin has been administered following hypovolemic shock. 2-O-desulfated NAC heparin was prepared as described in Example 1, and was used in the experiments at 7 mg/kg/h.

Figure 1A:
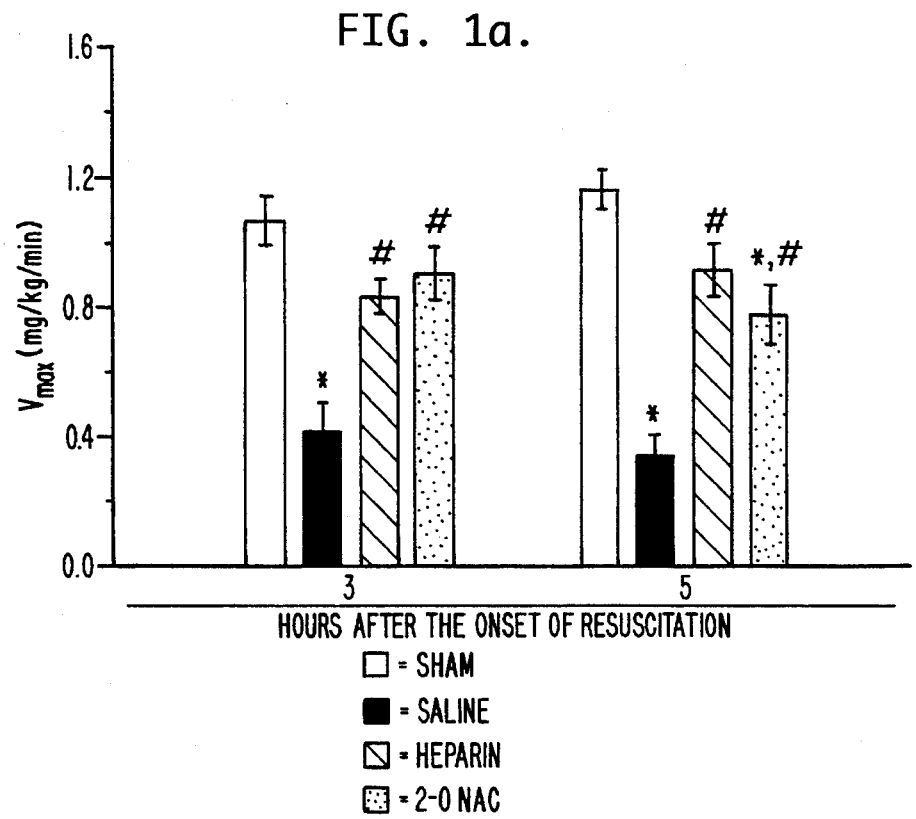
FIG. 1A is a bar graph showing changes in maximal velocity ($V_{max}$) of the clearance of indocyanine green (ICG) (active transport process) in sham-operated (Sham), normal saline-treated (Saline), heparin-treated (Heparin), and 2-O-desulfated NAC heparin treated rats at 3 and 5 h after the initiation of crystalloid resuscitation following hemorrhage. There were 6 animals in each group. The trauma-hemorrhage and resuscitation protocol and heparin or modified heparin III infusion procedure is described in Example 3. Data are presented as means ±SE and compared by one-way ANOVA and Tukey's test. *$P<0.05$ as compared with sham-operated group; #$P<0.05$ as compared with saline-treated group.
Figure 1B:
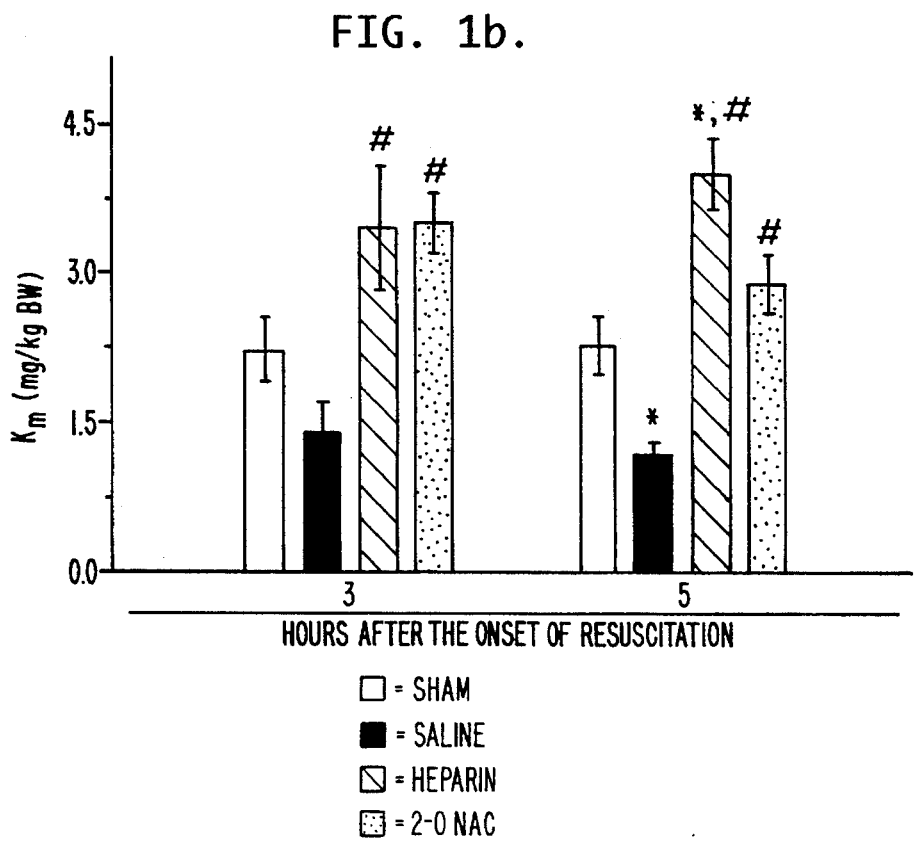
FIG. 1B is a bar graph showing changes in the efficiency ($K_m$) of the indocyanine green (ICG) transport in sham-operated (Sham), normal saline-treated (Saline), heparin-treated (Heparin), and 2-O-desulfated NAC heparin treated rats at 3 and 5 h after the initiation of crystalloid resuscitation. See the legend to FIG. 1A for further details.
Figure 2A:
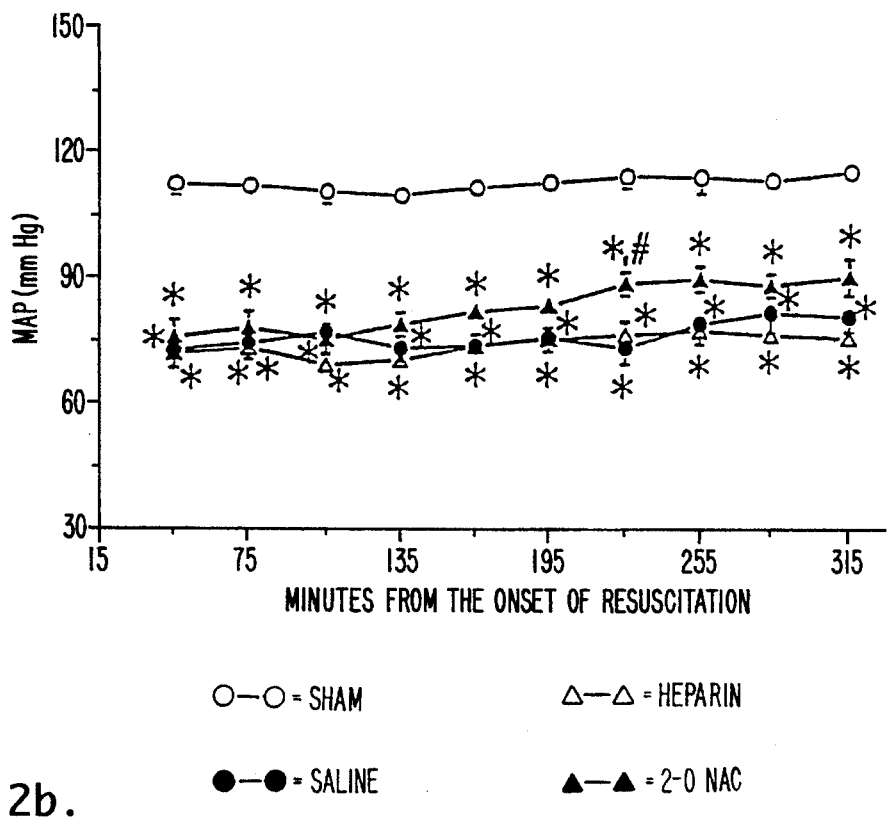
FIG. 2A is a graph showing changes in mean arterial pressure (MAP) in sham-operated (Sham), normal saline-treated (Saline), heparin-treated (Heparin), and 2-O-desulfated NAC heparin treated rats at 3 and 5 h after the initiation of crystalloid resuscitation. The trauma-hemorrhage/resuscitation protocols, diltiazem administration, and cardiac output (CO) measurements are described under Materials and Methods. "ON" and "OFF" denotes the beginning and the completion of infusion of 1 ml normal saline, heparin, or 2-O-desulfated NAC heparin solution. There were 6 animals in each group. The trauma-hemorrhage and resuscitation protocol and heparin or 2-O-desulfated NAC heparin infusion procedure is described in Example 3. Data are presented as means ±SE and compared by one-way ANOVA and Tukey's test. *$P<0.05$ as compared with sham-operated group; #$P<0.05$ as compared with saline-treated group.
Figure 2B:
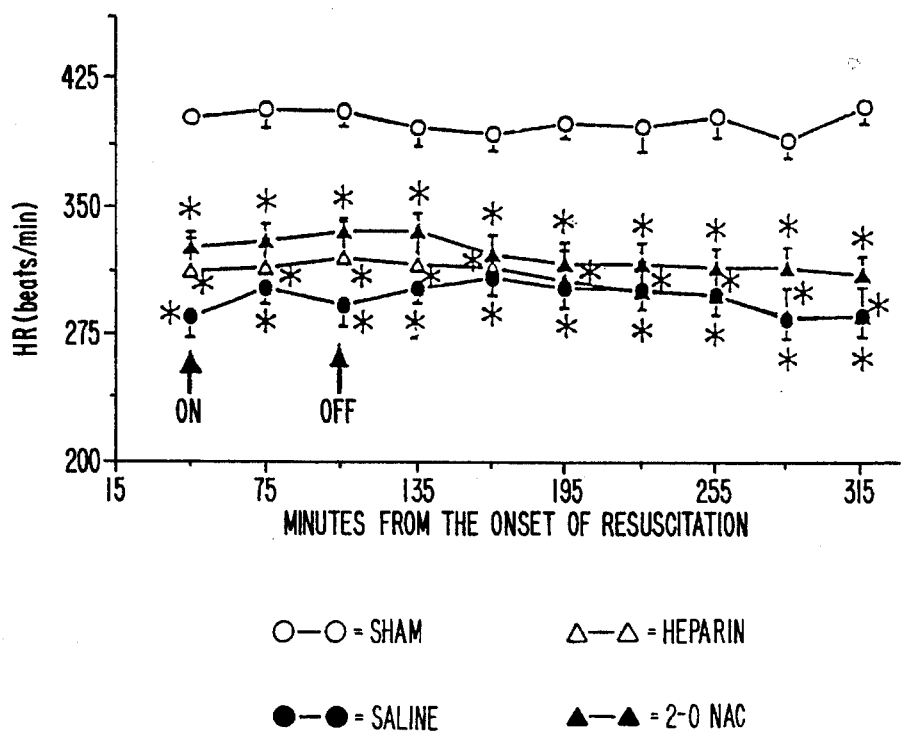
FIG. 2B is a graph showing changes in heart rate (HR) in sham-operated (Sham), normal saline-treated (Saline), heparin-treated (Heparin), and 2-O-desulfated NAC heparin treated rats at 3 and 5 h after the initiation of crystalloid resuscitation. See the legend to FIG. 2A for further details.
Figure 3A:
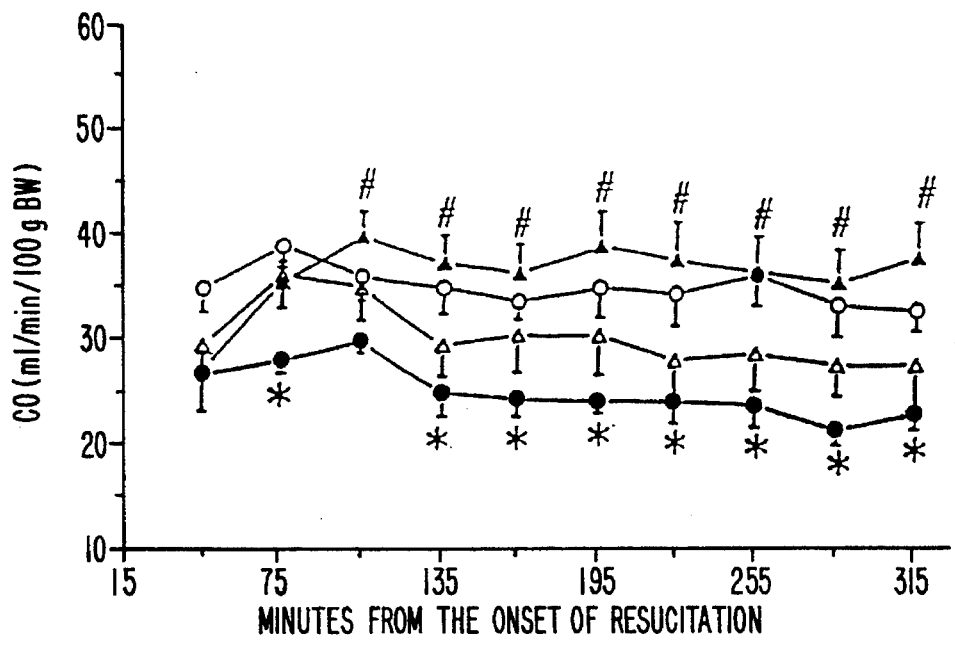
FIG. 3 includes graphs A, B and C showing changes in cardiac output (CO, A), stroke volume (SV, B), and total peripheral resistance (TPR, C) in sham-operated (Sham), normal saline-treated (Saline), heparin-treated (Heparin), and 2-O-desulfated NAC heparin treated rats at 3 and 5 h after the initiation of crystalloid resuscitation. See the legend to FIG. 2A for further details.
Figure 3B:
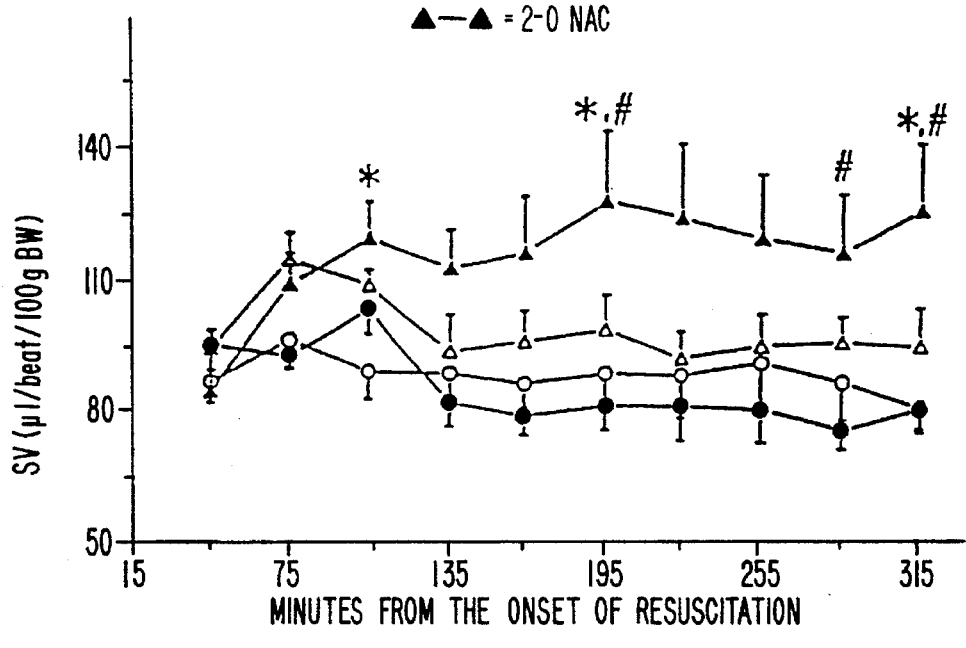
Figure 3C:
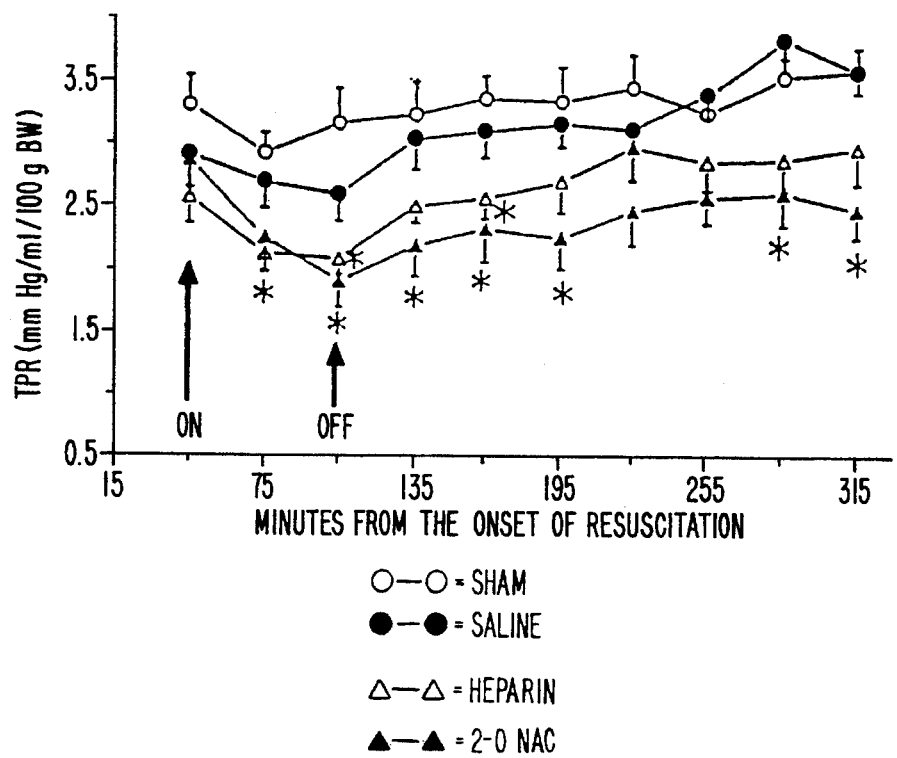
Figure 4A:
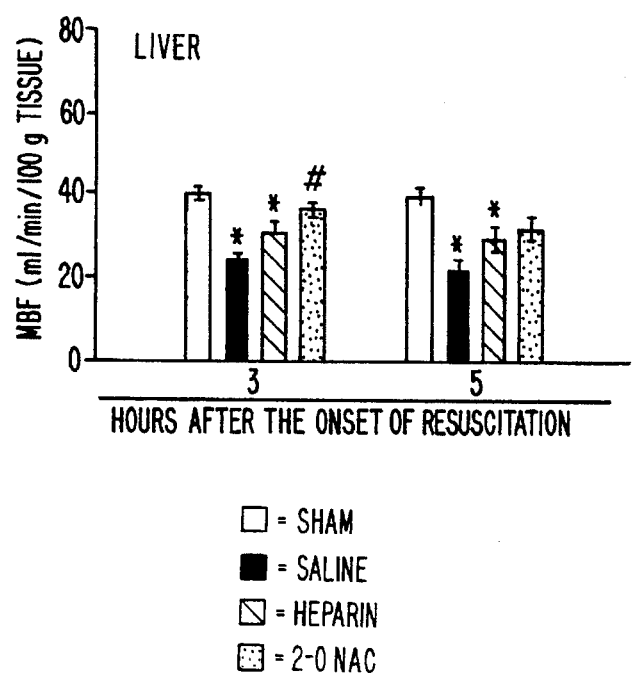
FIG. 4 includes graphs A, B, C and D showing changes in organ surface microvascular blood flow (MBF) in the liver (A), Kidney (B), spleen (C), and small intestine (D) in sham-operated (Sham), normal saline-treated (Saline), heparin-treated (Heparin), and 2-O-desulfated NAC heparin treated rats at 3 and 5 h after the initiation of crystalloid resuscitation. See the legend to FIG. 2A for further details.
Figure 4B:
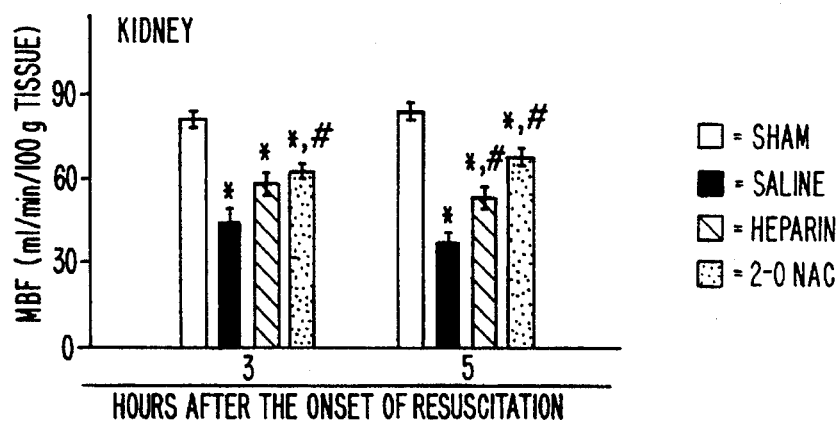
Figure 4C:
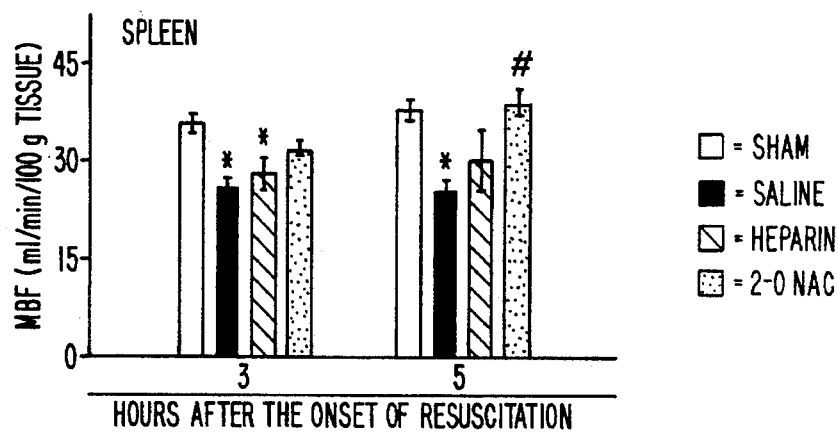
Figure 4D:
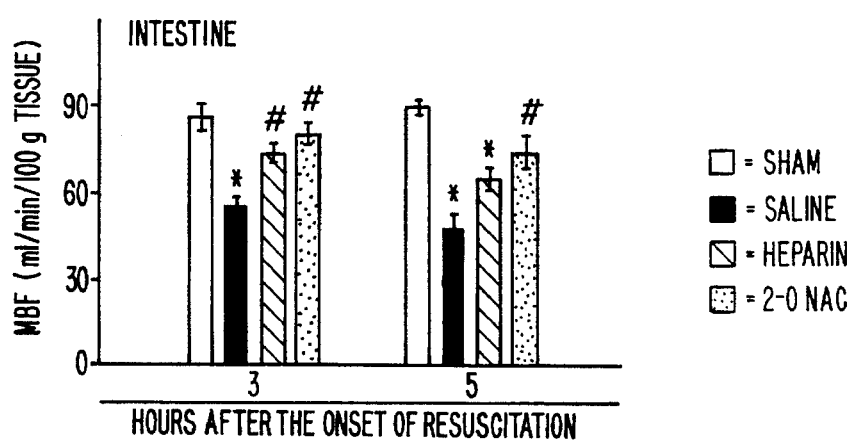
Figure 5A:
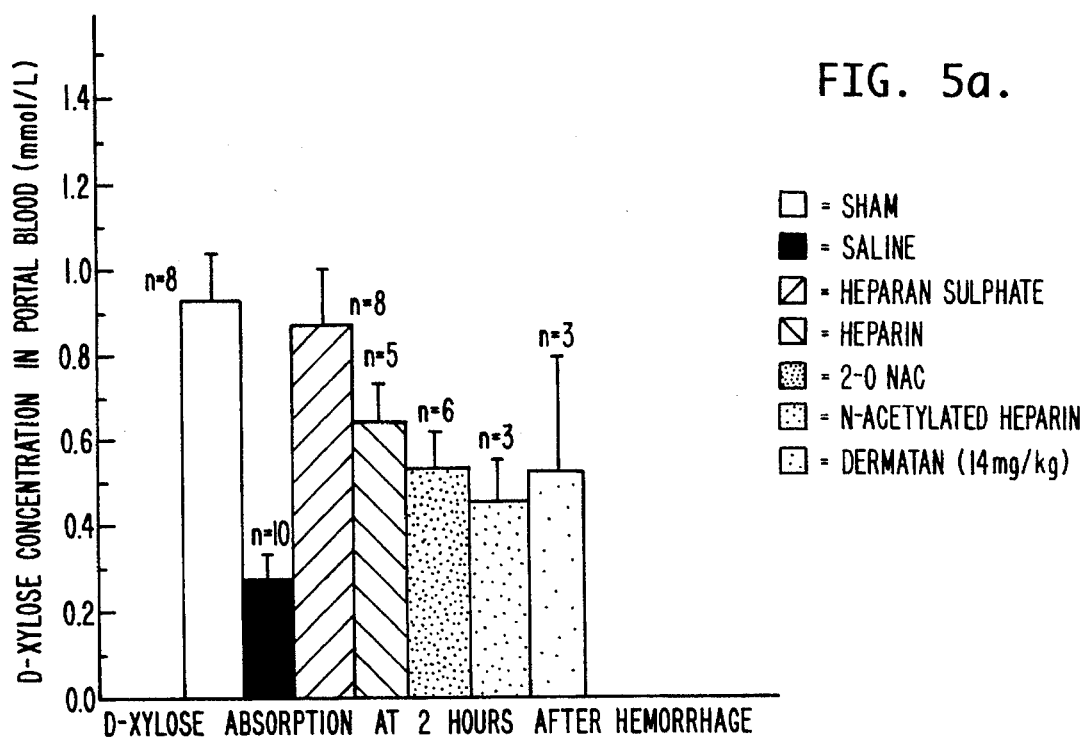
FIG. 5A is a graph of changes of D-xylose absorption 2 hours after sham-operation (Sham), normal saline-treated (Saline), heparin treated (Heparin), heparin sulfate-treated (Heparin sulfate), dermatan-treated, 2-O-desulfated NAC hepafin, and N-acylated heparin treated (N-acylated heparin) animals following hemorrhage and resuscitation.
Figure 5B:
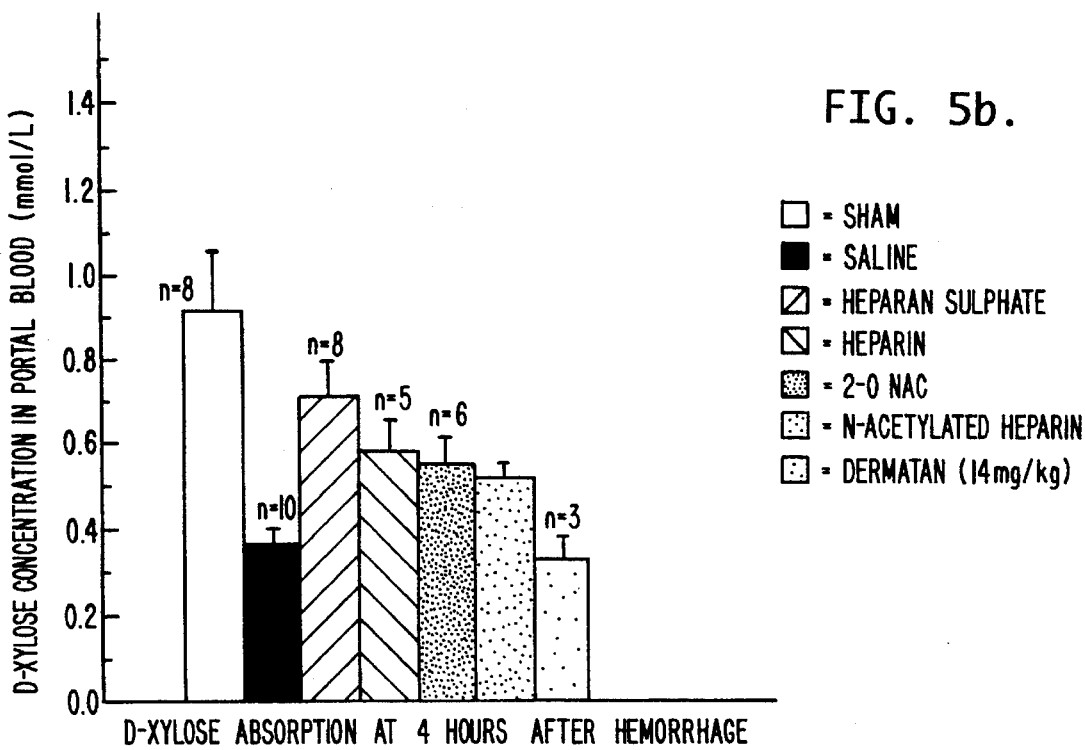
FIG. 5B is a graph of D-xylose absorption 4 hours after hemorrhage of the same general type as in FIG. 5A.

In this model, rats were bled and maintained at a mean arterial pressure (MAP) of 40 mm Hg, until 40% of the shed blood volume had been returned in the form of Ringers lactate (RL). The rats were then resuscitated with tour times the volume (~45 ml/rat) of maximum bleedout (MB) with RL over 60 min. via a jugular catheter and the following parameters were monitored: (1) hepatocellular function ($K_m$ and $V_{max}$ associated with indocyanine green clearance in (FIGS. 1A and B); (2) mean arterial pressure (MAP) and heart rate (HR) (FIGS. 2A and B); cardiac function {cardiac output (CO), stroke volume (SV) and total peripheral resistance (TPR) FIGS. 3A, B and C}; (4) microvascular blood flow (MBF) in liver, kidney, spleen and small intestine (FIGS. 4A, B, C and D, respectively); and (5) gut function (xylose absorption in FIGS. 5A and B). In FIGS. 1–5, data are presented for/bur different experimental groups consisting of (1) sham operated (positive control), (2) saline treated (negative control), (3) heparin treated, and (4) NAC treated.

Hepatocellular function was monitored using indocyanine clearance kinetics, where the $K_m$ and $V_{max}$ correlate with the efficiency of active transport, and rate of clearance, respectively. The maximal clearance rate ($V_{max}$, FIG. 1) at 3 h after initiating resuscitation was higher in the NAC group than the saline group, and was about 85% of sham level. The effect was slightly lower at 5 h, but still two-fold that of saline treated animals. The efficiency of active transport ($K_m$) at 3 h for the heparin and NAC group was higher (150–160%) than in the sham group. At 5 h the NAC group had decreased (125%) to values nearer sham while the heparin group remained elevated.

Cardiac function of the NAC group was improved relative to saline treated negative control animals, and to animals treated with heparin. The mean arterial pressure (FIG. 2A) for both saline and heparin treated animals climbed only slightly from 70 to about 75 mm Hg, while the NAC group climbed steadily from 70 to 90 mm Hg and the sham group was steady at about 110 mm Hg. Heart rate (FIG. 2B) for the NAC group was slightly higher during resuscitation, and remained elevated relative to heparin and saline treated animals, but lower than sham. Cardiac output (FIG. 3A) in the NAC group was increased to levels exceeding the sham control, over 5 h following hypovolemic shock, while the heparin group restored CO to 80% of sham group. Stroke volume (FIG. 3B) for the NAC animal group increased to levels higher than saline, heparin and sham groups. TPR (FIG. 3C) was lower following resuscitation in NAC and heparin groups versus saline treatment, although TPR increased more rapidly for the heparin treated animals after resuscitation, while the NAC group had lasting effects out to 5 h. Overall, these results support restored cardiac function in the NAC and heparin group, while the NAC group demonstrate uniquely improved CO and SV and TPR.

The microvascular blood flow (MBF) was measured at 3 h and 5 h after onset of resuscitation, as shown in FIG. 4A–D. All the data show the NAC group to have MBF elevated relative to the saline group, and the same or higher than heparin. Generally, the MBF recovered to within 80–100% of sham using NAC versus 50–60% for saline and 65–85% for heparin. Of the organs examined, the kidney showed poorest recovery; however, it is normal to see lagging recovery for this organ.

In the measurement of gut function, the NAC heparinoid showed an increase of 100% relative to the saline group, but was still only 55% of sham group at 2 h after hemorrhage. Heparin had a similar effect, while heparan sulfate had a greater effect. At 4 h after resuscitation, the heparinoid group maintained its level of absorption, while the heparin and heparan sulfate groups declined somewhat from their 2 h value.

These results demonstrate that the 2-O-desulfated heparin derivative (NAC) can exhibit effects equivalent to or greater than heparin in evaluations of cardiovascular function following hypovolemic shock. In gut function studies, the NAC was slightly less effective at 2 h after resuscitation, but was equally effective at 4 h. The equivalent or superior activity of the NAC relative to heparin is surprising in light of its different chemical composition and biological activities. Specifically, unlike native heparins and heparin-like molecules (i.e. heparan sulfate), the chemically modified NAC has lower anticoagulant activity and bleeding effects, thus reducing the hematological toxicities typically associated with heparin, and allowing higher doses to be utilized. Most importantly, the biological properties of the NAC pertinent to the hypovolemic shock model are not affected by the structural modification or the resultant alteration of the spectrum of biological activities.

Example 3

Effect of 2-O, 3-O Desulfated NAC Heparin Fragments on Hemodynamics and Hepatocellular Function Trauma-Hemorrhage and Resuscitation (Rs)

2-O, 3-O desulfated NAC heparin fragments were produced substantially as described in U.S. patent Ser. No. 944,804, filed Dec. 22, 1992. However, fragments having an average molecular weight of 3–4 kDa were desulfated in lieu of fragments with an average molecular weight of 5 kDa. Briefly, 1.0 g of low molecular weight (5 kDa) hog mucosal heparin, obtained from Celsus Laboratories, was dissolved in 200 ml of 0.1M sodium hydroxide solution. The solution was frozen and lyophilized to dryness, yielding a crusty yellow colored residue. The residue was dissolved in 50 ml of water and the solution adjusted to pH 6–7 by the addition of 20% acetic acid solution. Solid sodium bicarbonate was then added to bring the pH up to 8–9. The solution was exhaustively dialyzed and after lyophilization was isolated as a solid product (0.77 g). The % anticoagulant activity was <2. IdoA 2-S and $GMS_2$ were not detectable, indicating that the heparin starting material is >95 or 99% desulfated. The NAC composition was used at 7 mg/kg/h).

Figure 6A:
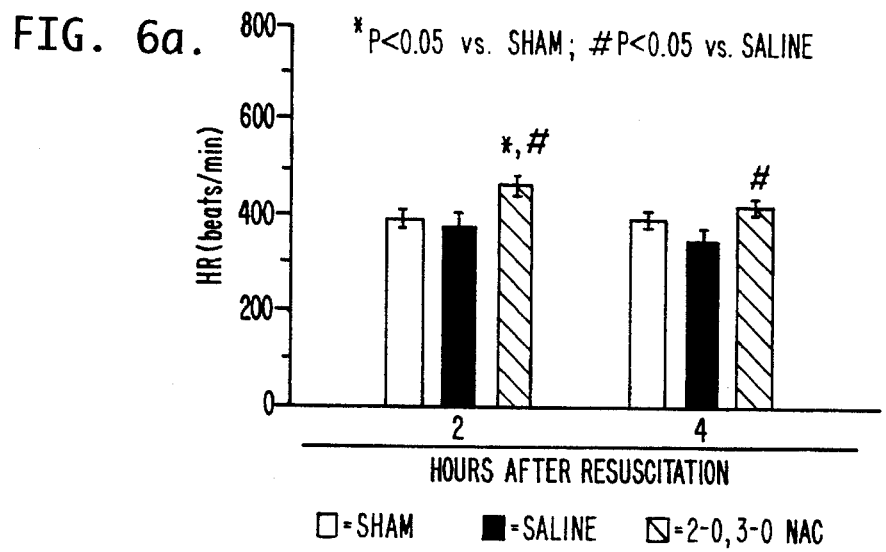
FIG. 6 shows changes in heart rate (HR, A) stroke volume (SV, B) and cardiac output (CO, C), in sham operated (Sham), normal saline-treated (Saline), and 2-O, 3-O desulfated NAC heparin treated groups at 2 and 4 hours after the end of resuscitation with lactated Ringers. Each group consisted of 6 animals. Data are represented as means ±SE and compared by one-way ANOVA and Tukey's test.
Figure 6B:
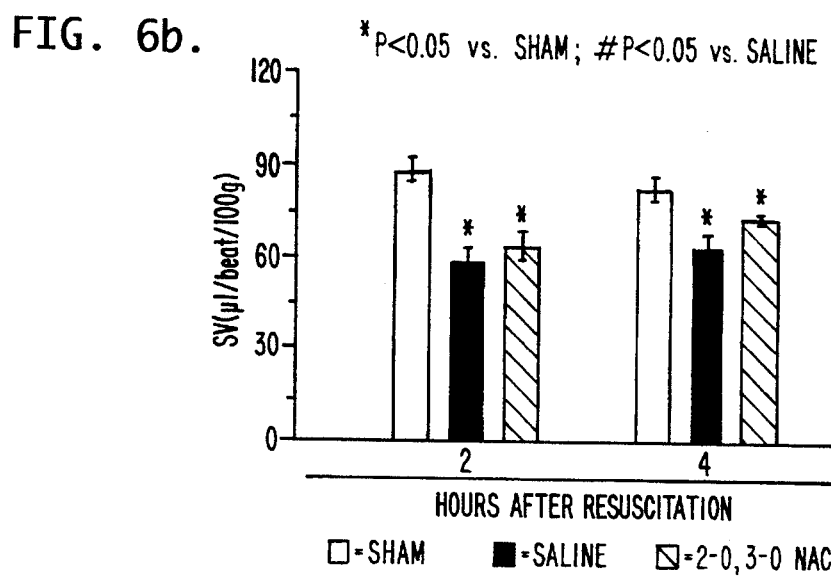
Figure 6C:
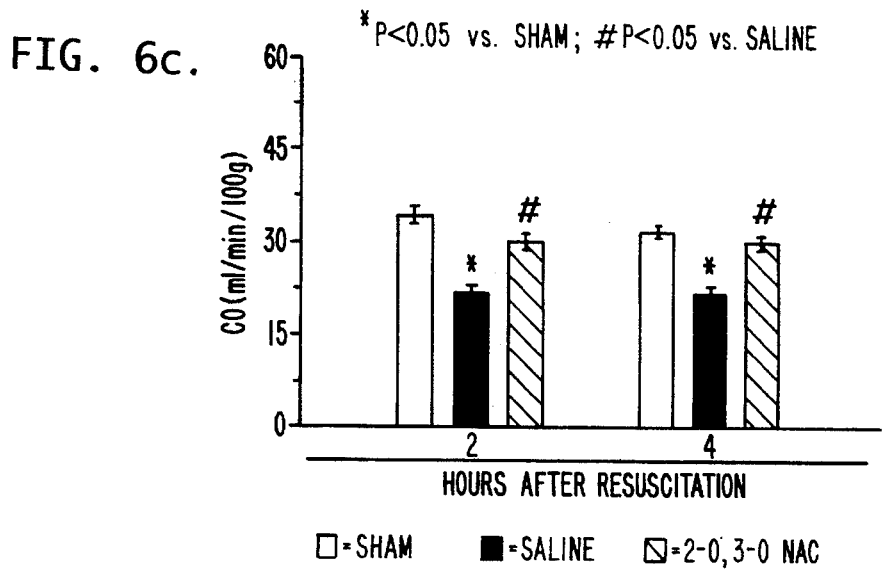
Figure 7A:
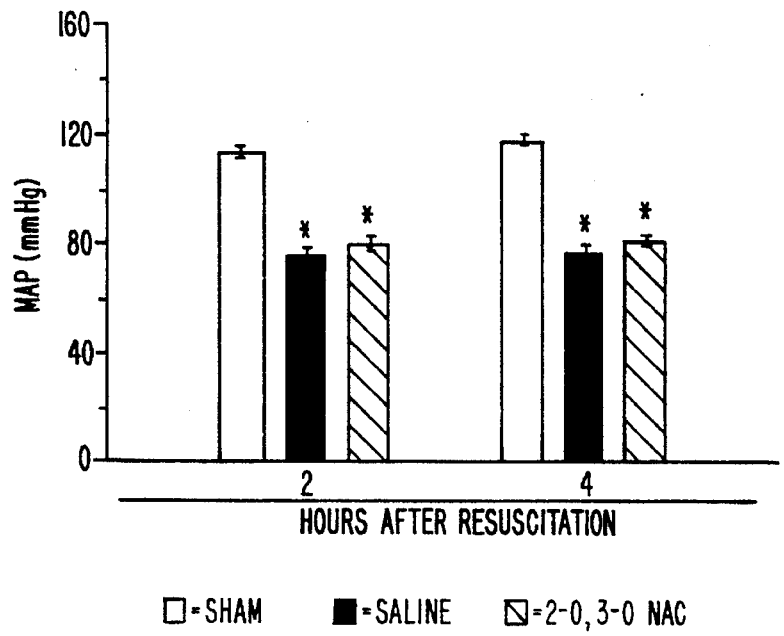
FIG. 7 shows changes in mean arterial pressure (MAP, A) and total peripheral resistance (TPR, B) in sham operated (Sham), normal saline-treated (Saline), and 2-O, 3-O desulfated NAC heparin treated groups at 2 and 4 hours after the end of resuscitation with lactated Ringers. Each group consisted of 6 animals. Data are represented as means ±SE and compared by one-way ANOVA and Tukey's test.
Figure 7B:
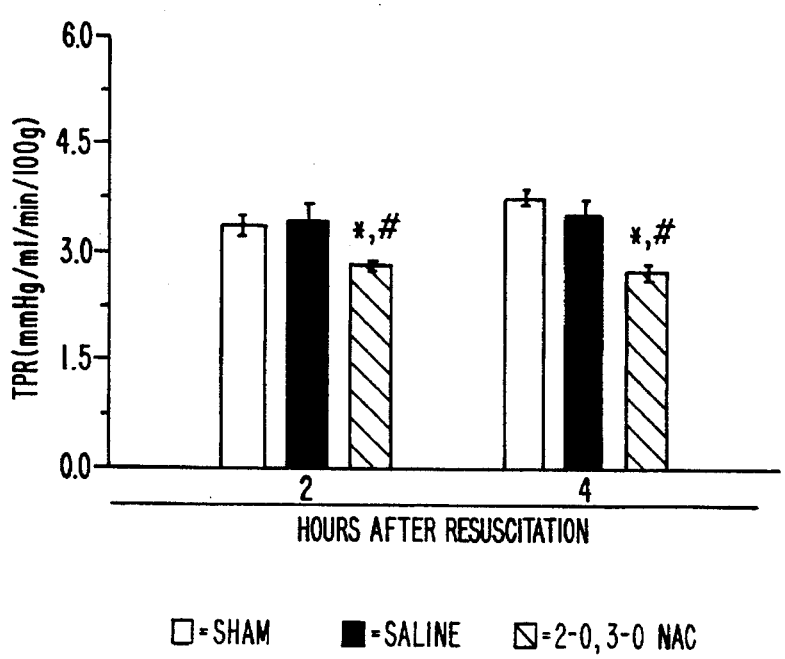
Figure 8A:
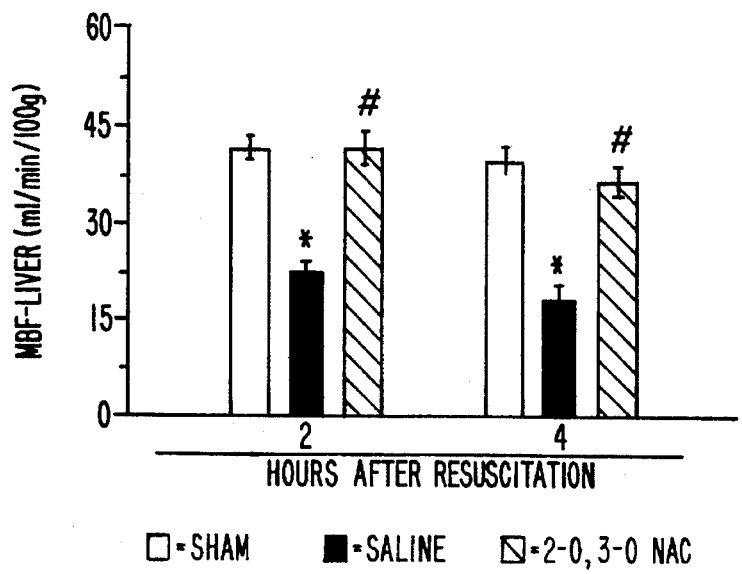
FIG. 8 shows changes in organ surface microvascular blood flow (MBF) in the liver (A), kidney (B), spleen (C) and gut (D), in sham operated (Sham), normal saline-treated (Saline), and 2-O, 3-O desulfated NAC heparin treated groups at 2 and 4 hours after the end of resuscitation with lactated Ringers. Each group consisted of 6 animals. Data are represented as means +SE and compared by one-way ANOVA and Tukey's test.
Figure 8B:
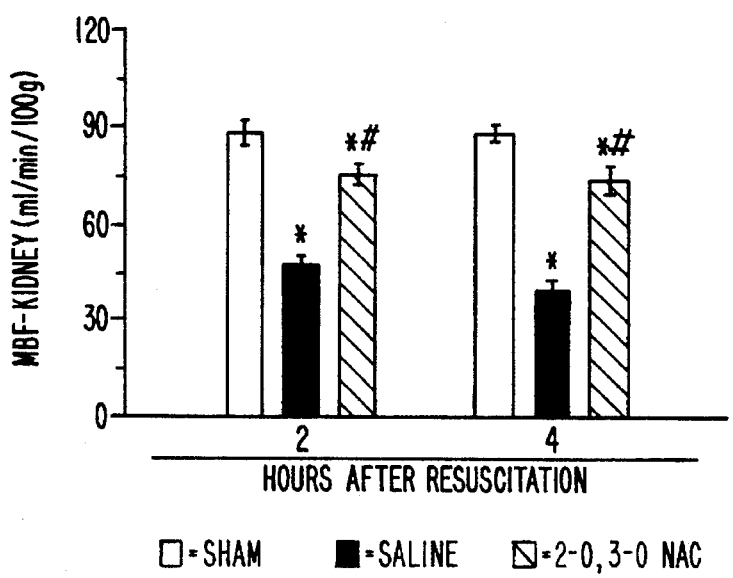
Figure 8C:
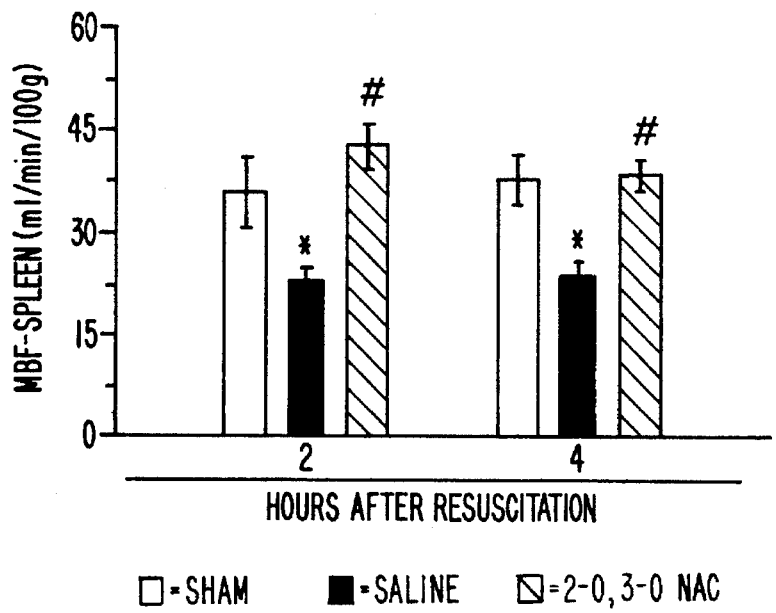
Figure 8D:
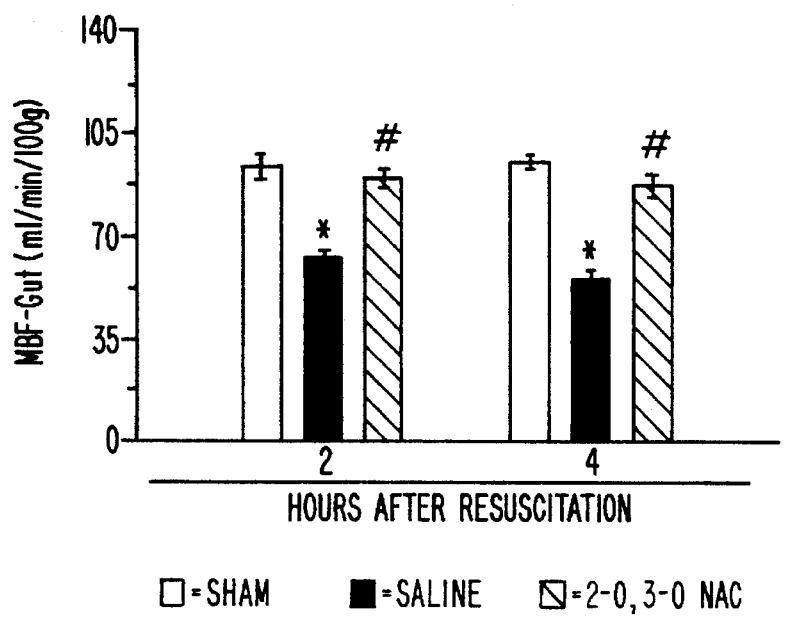

Cardiac function of the 2-O, 3-O-desulfated NAC treated group (7 mg/kg/h) was significantly improved relative to saline treated control animals. Heart rate (FIG. 6A) for the NAC group was slightly higher at 2 h after resuscitation, and decreased back to sham levels by 4 h. Stroke volume (FIG. 6B) for the NAC animal group was not significantly higher than the saline group and only slightly lower than sham groups. Cardiac output (FIG. 6C) in the NAC group was increased to levels almost equivalent to sham control, over 4 h following hypovolemic shock. The mean arterial pressure (FIG. 7A) for both saline and NAC treated animals were about 70 to about 75 mmHg compared to sham group having MAP of about 110 mmHg. The total peripheral resistance (TPR) (FIG. 7B) was lowered in NAC group vs saline treatment after resuscitation, and had lasting effects out to 4 h. Overall, these results support restored cardiac function in the NAC and heparin group, while the NAC group demonstrated uniquely improved CO and SV and TPR.

The microvascular blood flow (MBF) in the liver, kidney, spleen and intestine was measured at 2 and 4 h after completion of resuscitation, as shown in FIG. 8A–D, respectively. The data show that the NAC treated group have elevated MBF relative to the saline group, and almost equivalent to the sham group in all organs tested. Generally, the MBF recovered to within 90–100% of sham using NAC versus 50–60% for saline.

Figure 9A:
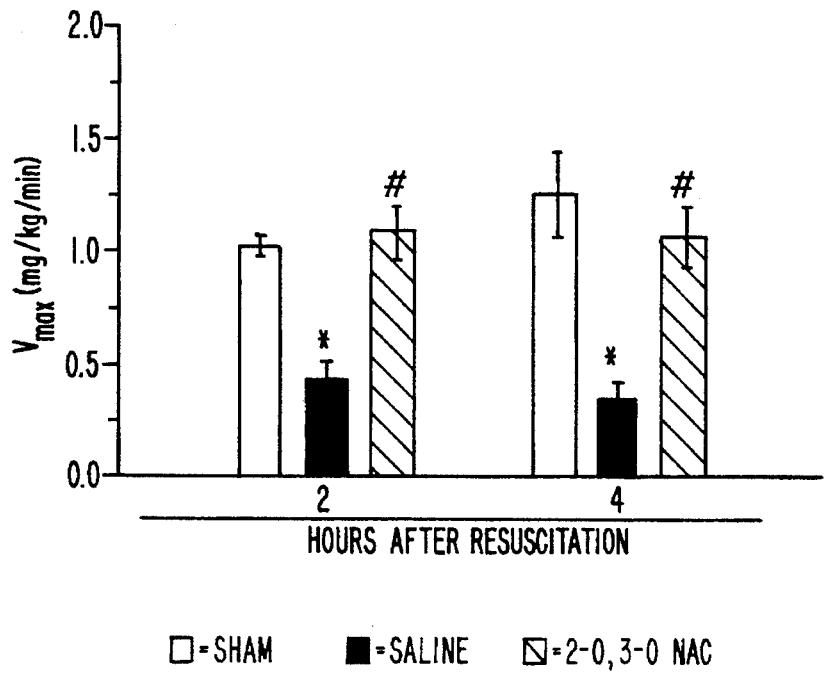
FIG. 9 shows changes in liver function as measured by alterations in maximal velocity ($V_{max}$, A) and the efficiency of transport ($K_m$, B) of the indocyanine green (ICG) clearance in sham operated (Sham), normal saline-treated (Saline), and 2-O, 3-O desulfated NAC heparin treated groups at 2 and 4 hours after the end of resuscitation with lactated Ringers. Each group consisted of 6 animals. Data are represented as means ±SE and compared by one-way ANOVA and Tukey's test.
Figure 9B:
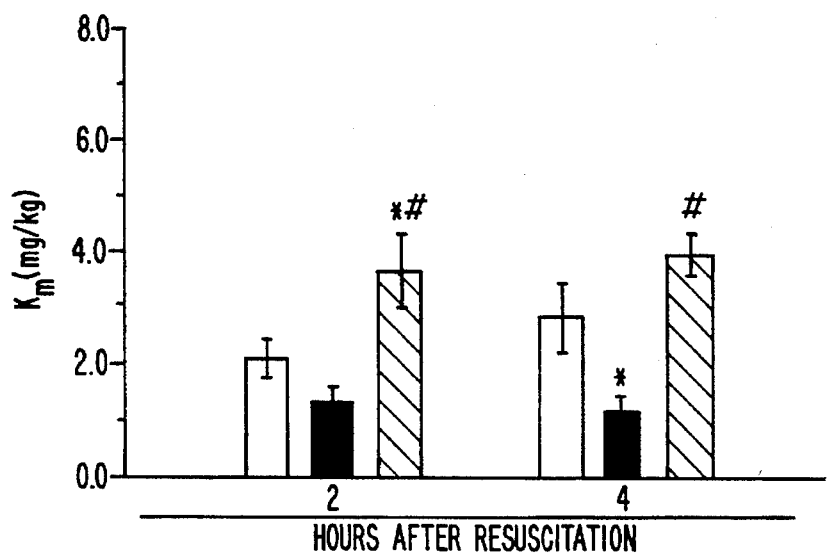

Hepatocellular function was monitored using indocyanine clearance kinetics, where the $V_{max}$ and $K_m$ correlate with the efficiency of active transport, and rate of clearance, respectively (see FIG. 9A and 9B, respectively). The maximal clearance rate (Vmax) at 2 h after completing resuscitation was higher in the NAC group than the saline group, and was equivalent to sham level. The effect was slightly lower at 4 h, but was 90% of sham and three fold that of saline treated animals. The efficiency of active transport (Km) at 2 h for the NAC group was higher (~200%) than in the sham group.

At 4 h the NAC group had decreased to values nearer sham (125%).

Figure 10:
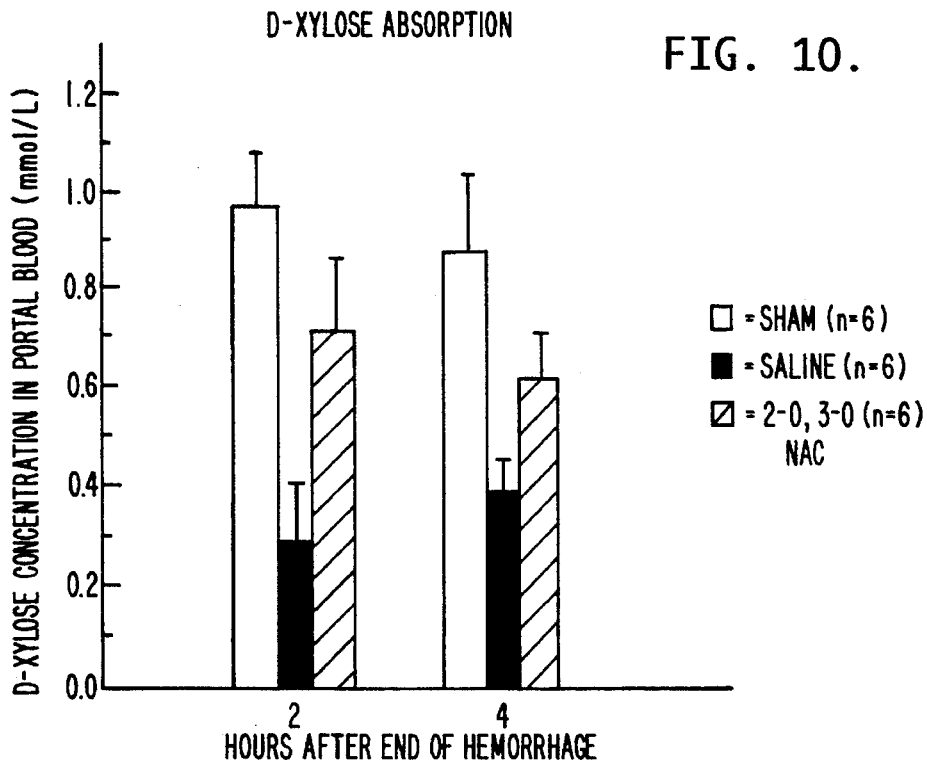
FIG. 10 shows changes in gut function as measured by xylose absorption in sham operated (Sham), normal saline-treated (Saline), and 2-O, 3-O desulfated NAC heparin treated groups at 2 and 2 hours after the end of resuscitation with lactated Ringers. Each group consisted of 6 animals. Data are represented as means ±SE and compared by one-way ANOVA and Tukcy's test.

In the measurement of gut function (FIG. 10), NAC increased to 70% relative to the sham group versus only 55% for the saline group. At 4 h after resuscitation the gut function declined somewhat from the 2 h value, and was about 60% of the sham group, while the saline group was 40% of the sham group.

Example 4

Effects of 2-O, 3-O Desulfated Substantially intact NAC Heparin on Hemodynamics and Hepatocellular Function after Trauma-Hemorrhage and Resuscitation (Rs)

2-O, 3-O desulfated heparin is produced substantially as described in U.S. patent Ser. No. 944,804, filed Dec. 22, 1992. Briefly, 1.0 g of Ming Han hog mucosal heparin is dissolved in 180 ml of water and 20 ml of 1M NaOH is added to make the solution 0.1M in NaOH, and 0.5% in heparin. The solution is frozen and lyophilized to dryness. The resulting crusty yellow colored residue is dissolved in 50 ml of water and then adjusted to pH 6–7 by the addition of 20% acetic acid solution. Solid sodium bicarbonate is added to bring the pH up to 8–9. The solution is exhaustively dialyzed and lyophilized thereby yielding 0.73 g of solid product.

The product is subjected to various assays, including a determination of aPTT values, and disaccharide analysis. The values presented are relative to the heparin starting material. A commercial kit obtained from Baxter laboratories is used to determine aPTT values. The manufacture's instructions regarding the use of the kit are followed. The values are expressed as the % aPTT relative to heparin.

Using these assays the product isolated as described above exhibited the following % anticoagulant activity (aFTT), IdoA 2-S, and $GMS_2$, respectively; 10.0, 1.1, and <1. The 2-O, 3-O desulphated NAC was used at a concentration of 7 mg/kg/h.

The physiological parameters measured in the previous example are similarly measured for the 2-O, 3-O desulfated substantially intact NAC.

Regarding cardiac function, 2-O, 3-O desulfated substantially intact NAC treated group (7 mg/kg//h) would show marked improvement relative to saline treated control animals. Heart rate for the NAC group is slightly higher at 2 h after resuscitation, and decreases back to sham levels by 4 h. Stroke volume for the NAC animal group is not significantly higher than the saline group and only slightly lower than sham groups. Cardiac output in the NAC group is increased to levels almost equivalent to sham control, over 4 h following hypovolemic shock. The mean arterial pressure for both saline and NAC treated animals would be about 70 to about 75 mm Hg compared to sham group having MAP of about 110 mmHg. The total peripheral resistance (TPR) is lowered in the NAC group vs saline treatment after resuscitation, and has lasting effects out to 4 h. Overall, these results would support restored cardiac function in the NAC and heparin group, while the NAC group demonstrates uniquely improved CO and SV and TPR.

The microvascular blood flow (MBF) in the liver, kidney, spleen and intestine is measured at 2 and 4 h after completion of resuscitation. The data would show that the NAC treated group has elevated MBF relative to the saline group, and almost equivalent to the sham group in all organs tested. Generally, the MBF recovers to within 90–100% of sham group using NAC versus 50–60% for saline. Heparin is known to restore about 65–70% of sham MBF.

Regarding, hepatocellular function the maximal clearance rate (Vmax) at 2 h after completing resuscitation would be higher in the NAC group than the saline group, and equivalent to sham level. The effect is slightly lower at 4 h, but was 90% of sham and three fold that of saline treated animals. The efficiency of active transport (Km) at 2 h for the NAC group is higher (~200%) than in the sham group. At 4 h the NAC group values decrease to values nearer the sham group(125%).

As for gut function, the NAC values increase to 70% relative to the sham group versus only 55% for the saline group. At 4 h after resuscitation the gut function declines somewhat from the 2 h value, and is about 60% of the sham group, while the saline group is 40% of the sham group.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

Example 5

Effects of 2-O, 3-O Desulfated NAC Heparin Fragments on the Survivability of Rats Following Hemorrhage An additional experiment was performed to ensure that 2-O, 3-O desulphated NAC fragments improve cardiovascular and hepatocellular function following trauma-hemorrhage. Furthermore, the experiment was designed to test whether this composition decreases susceptibility to sepsis which often accompanies trauma-hemorrhage.

2-O, 3-O desulphated NAC fragments were produced as described in Example 3, and used at a concentration of 7 mg/kg/h. The experiment was run as shown in FIG. 11. As in the previous examples, the rats were divided into three groups: sham-operated, saline-treated, and 2-O, 3-O desulfated NAC fragment treated animals. The rats underwent laparotomy and were bled to and maintained at a mean blood pressure of 40 mmHg until 40% of maximal bleedout volume was returned in the form of Ringers Lactate. The rats were next rescusitated with three times the volume of shed blood with Ringers Lactate over 45 minutes, followed by infusion of two times Ringer Lactate plus 2-O, 3-O desulphated NAC fragments or normal saline over 60 minutes. At two and four hours after resuscitation, cardiac output (CO:ml/min/100 g) was measured by indocyanine green (ICP) soluton while a heptocellular function [i.e., maximum velocity of ICG clearance ($V^{max}$;mg/kg/min)] was determined using an in vivo ICG clearance technique. Microvascular blood flow (MBF:ml/min/100 g) was assessed by laser Doppler flowmetery. Lastly, sepsis was induced by cecal ligation and puncture 20 hours after hemorrhage and the nectrotic cecum was excised 10 hours later.

The results are shown in the following table:

TABLE 1

|  | Sham-Operated | | Saline-Treated | | 2-0, 3-0-NAC Treated | |
| --- | --- | --- | --- | --- | --- | --- |
|  | 2 h | 4 h | 2 h | 4 h | 2 h | 4 h |
| CO | 34 ± 2 | 32 ± 1 | 22 ± 1* | 22 ± 1* | 30 ± 1# | 30 ± 1# |
| Vmax | 1.0 ± .1 | 1.3 ± .2 | 0.5 ± .1* | 0.4 ± .1* | 1.1 ± .1# | 1.1 ± 1# |
| MBF-Liver | 42 ± 2 | 40 ± 2 | 23 ± 1* | 18 ± 2* | 42 ± 2# | 37 ± 2# |
| Spleen | 36± | 38 ± 6 | 24 ± 1* | 25 ± 2* | 43 ± 3# | 39 ± 2# |
| Intestine | 94 ± 4 | 96 ± 2 | 64 ± 1* | 58 ± 3* | 90 ± 3# | 88 ± 4# |

(N = 6–7; mean ± SB; one-way ANOVA and Tukey's test: *$P < 0.05$ vs Sham; #$P < 0.05$ vs Saline)

It is clear from the data in the table that both cardiac output and hepatocellular function in rats treated with 2-O, 3-O desulphated NAC fragments are similar to sham-operated animals. Microvascular blood flow was also similar for 2-O, 3-O desulphated NAC treated rats compared to sham-operated rats. However, it is important to note that for the parameters tested, either at two or four hours, saline-treated rats showed considerable deterioration.

Most interesting, was the observation that the mortality rate in sham-operated rats and saline-treated animals was 0% and 83% ($P \leq 0.05$; n=12/group) respectively, while rats treated with 2-O, 3-O desulphated NAC fragments exhibited a much reduced mortality of 44% ($P \leq 0.05$ vs. hemorrhage, n=16)(FIG. 12).

This experiment shows that 2-O, 3-O desulphated NAC fragments restore cardiovascular, hepatocellular, and microcirculatory function, and moreover, decreases mortality to sepsis related to this procedure.

What is claimed is:

1. A method for treating hypovolemic shock in an animal, comprising administering to said animal a therapeutically effective amount of an O-desulfated heparinoid composition that is at least about 85% non-anticoagulant.

2. The method according to claim 1 wherein said heparinoid composition comprises an intact polymer.

3. The method according to claim 1 wherein said heparinoid composition comprises therapeutically effective fragments of said heparinoid.

4. The method according to claim 3 wherein said fragments have an average molecular weight of about 2 to about 6.4 kDa.

5. The method according to claim 1 wherein said O-desulfated heparinoid comprises unfragmented 2-O desulfated heparin or a therapeutically effective fragment of 2-O desulfated heparin.

6. The method according to claim 1 wherein said O-desulfated heparinoid comprises unfragmented 2-O, 3-O desulfated heparin or a therapeutically effective fragment of 2-O, 3-O desulfated heparin.

7. The method according to claim 6 wherein said O-desulfated heparinoid is desulfnated at the 2-O and 3-O positions in amounts from approximately 50% to about 99% and from approximately 50% to about 75%, respectively.

8. A method according to claim 1 wherein the administration is intravenous.

9. The method according to claim 1 wherein said O-desulfated heparinoid is administered as an injectable pharmaceutical composition comprising an O-desulfated heparinoid that is at least about 85% non-anticoagulant in a pharmaceutically acceptable excipient.

10. The method of claim 9, wherein said heparinoid is administered in a therapeutically effective amount sufficient to improve microvascular blood flow in an organ selected from the group consisting of liver, kidney, spleen and small intestine.

11. The method of claim 9, wherein said heparinoid is administered without pre-heparinization of said animal.

12. A method for preventing sepsis in patients experiencing hypovolemic shock, comprising administering to said patients an effective amount of an O-desulfated heparinoid composition that is at least about 85% non-anticoagulant.

13. The method according to claim 12, wherein said O-desulfated heparinoid composition comprises an unfragmented heparinoid.

14. The method of claim 12, wherein said O-desulfated heparinoid composition comprises a therapeutically effective fragment of said heparinoid.

15. The method according to claim 12, wherein said O-desulfated heparinoid comprises unfragmented 2-O, 3-O desulfated heparin or a therapeutically effective fragment of 2-O, 3-O desulfated heparin.

16. The method according to claim 14, wherein said fragment is a 2-O, 3-O desulfated fragment.

17. The method of claim 9, wherein said O-desulfated heparinoid is administered in a therapeutically effective amount sufficient to prevent vascular damage.

18. The method of claim 9, wherein said O-desulfated heparinoid is administered in a therapeutically effective amount sufficient to improve organ function.

19. The method of claim 9, wherein said O-desulfated heparinoid is administered in a therapeutically effective amount sufficient to improve cardiac function.

* * * * *

UNITED STATES PATENT AND TRADEMARK OFFICE
CERTIFICATE OF CORRECTION

PATENT NO. : 5,583,121

DATED : December 10, 1996

INVENTOR(S) : Irshad H. Chaudry, et al.

It is certified that error appears in the above-identified patent and that said Letters Patent is hereby corrected as shown below:

Column 1, line 56, delete "AT-I11" and insert --AT-III--

Column 2, line 54, delete "tour" and insert --four--

Column 3, line 47, delete "(FRD" and insert --(I/RI)--

Column 7, line 13, delete "undepolymefized" and insert --unde-polymerized--

Column 7, line 24, delete "hepafin" and insert --heparin--

Column 8, line 37, delete "hepafin" and insert --heparin--

Column 9, line 13, delete "am" and insert --are--

Column 10, line 42, delete "hepafin" and insert --heparin--

Column 10, line 53, delete "79:1-7" and insert --79:1-17--

Column 11, line 31, delete "NAG" and insert --NAC--

Column 12, line 44, delete "Periin" and insert --Perlin--

Column 12, line 46, delete "arthydrides" and insert --anhydrides--

Column 12, line 48, delete "artionic" and insert --anionic--

Column 13, line 29, delete "transderrnal" and insert --transdermal--

Column 13, line 33, delete "grail" and insert --graft--

UNITED STATES PATENT AND TRADEMARK OFFICE
CERTIFICATE OF CORRECTION

PATENT NO. : 5,583,121

DATED : December 10, 1996

INVENTOR(S) : Irshad H. Chaudry, et al.

It is certified that error appears in the above-identified patent and that said Letters Patent is hereby corrected as shown below:

Column 14, line 55, delete "tour" and insert --four--

Column 14, line 67, delete "for/bur" and insert --for four--

Column 17, line 38, delete "(aFTT)" and insert --(aPTT)--

Column 19, line 9, (in TABLE 1, $V_{max}$ row and 4h column), delete "1.1±1#" and insert --1.1±.1#--

Column 19, line 9, (in legend for TABLE 1), delete "SB" and insert --SE--

Signed and Sealed this

Twenty-eighth Day of April, 1998

Attest:

Attesting Officer

BRUCE LEHMAN

Commissioner of Patents and Trademarks